(12) United States Patent
Nakai

(10) Patent No.: US 6,783,958 B2
(45) Date of Patent: Aug. 31, 2004

(54) METHOD OF PRODUCING A BIOSENSOR PROTEIN CAPABLE OF REGULATING A FLUORESCENCE PROPERTY OF GREEN FLUORESCENT PROTEIN, AND THE BIOSENSOR PROTEIN PRODUCED BY THE METHOD

(75) Inventor: Junichi Nakai, Okazaki (JP)

(73) Assignee: Okazaki National Research Institutes, Ohazaki (JP)

( * ) Notice: Subject to any disclaimer, the term of this patent is extended or adjusted under 35 U.S.C. 154(b) by 288 days.

(21) Appl. No.: 09/989,025

(22) Filed: Nov. 21, 2001

(65) Prior Publication Data

US 2003/0068674 A1 Apr. 10, 2003

(30) Foreign Application Priority Data

Nov. 22, 2000 (JP) ........................................ 2000-356047

(51) Int. Cl.[7] ............................................... C12P 21/06
(52) U.S. Cl. ....................................................... 435/69.1
(58) Field of Search ........................... 435/69.1, 320.1; 530/350; 424/192.1; 514/1; 536/23.4

(56) References Cited

U.S. PATENT DOCUMENTS 6,376,257 B1 * 4/2002 Persechini ................... 436/501

FOREIGN PATENT DOCUMENTS

| EP | 1 132 397 | 9/2001 |
|---|---|---|
| WO | WO 00/71565 | 11/2000 |

OTHER PUBLICATIONS

J. Nakai, et al., Nature Biotechnology, vol. 19, No. 2, pp. 137–141, "A High Signal–to–Noise $Ca^{2+}$ Probe Composed of a Single Green Fluorescent Protein", Feb. 2001.

G. S. Baird, et al., Proc. Natl. Acad. Sci. USA, vol. 96, No. 20, pp. 11241–11246, "Circular Permutation and Receptor Insertion within Green Fluorescent Proteins", Sep. 28, 1999.

N. Doi, et al., FEBS Letters, vol. 453, No. 3, pp. 305–307. "Design of Generic Biosensors Based on Green Fluorescent Proteins with Allosteric Sites by Directed Evolution", Jun. 25, 1999.

C. Scharnagl, et al., Biophysical Journal, vol. 77, No. 4, pp. 1839–1857. "Molecular Basis for pH Sensitivity and Proton Transfer in Green Fluorescent Protein: Protonation and Conformational Substates from Electrostatic Calculations". Oct. 1999.

* cited by examiner

*Primary Examiner*—Karen Cochrane
(74) *Attorney, Agent, or Firm*—Oblon, Spivak, McClelland, Maier & Neustadt, P.C.

(57) ABSTRACT

A biosensor protein comprising (1) and (2) below: (1) a modified fluorescent protein which is obtained by cleaving amino acid sequence of green fluorescent protein or its derivative in the vicinity of a hotspot amino acid residue which affects the fluorescence property, and modifying the structure of the green fluorescent protein or its derivative, and (2) one or more functional molecules which are capable of transmitting their conformational changes to the modified fluorescent protein to cause a conformational change of the modified fluorescent protein, thereby altering the fluorescence property of the modified fluorescent protein.

4 Claims, 3 Drawing Sheets

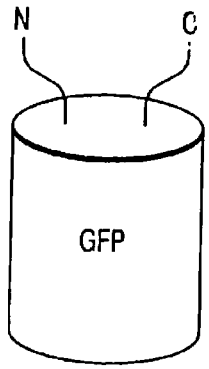
F I G. 1A
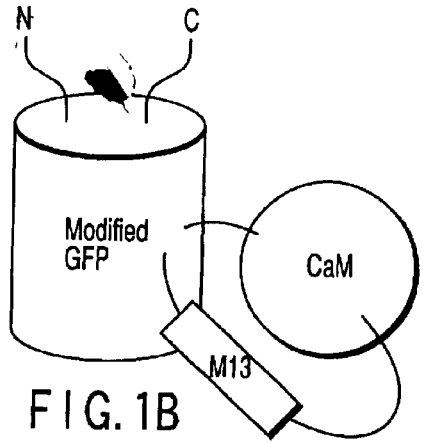
F I G. 1B
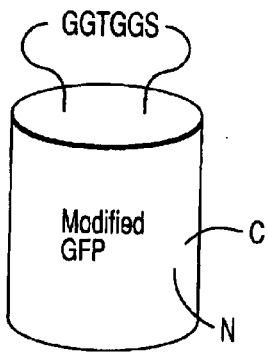
F I G. 1C
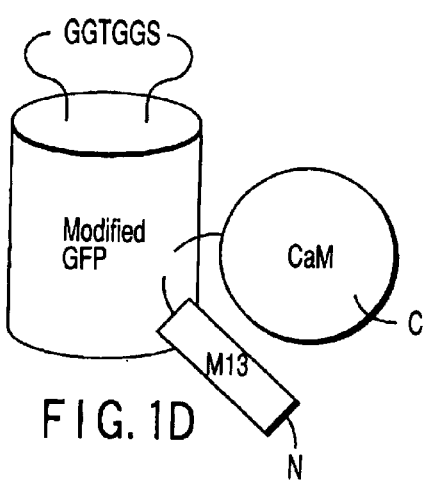
F I G. 1D
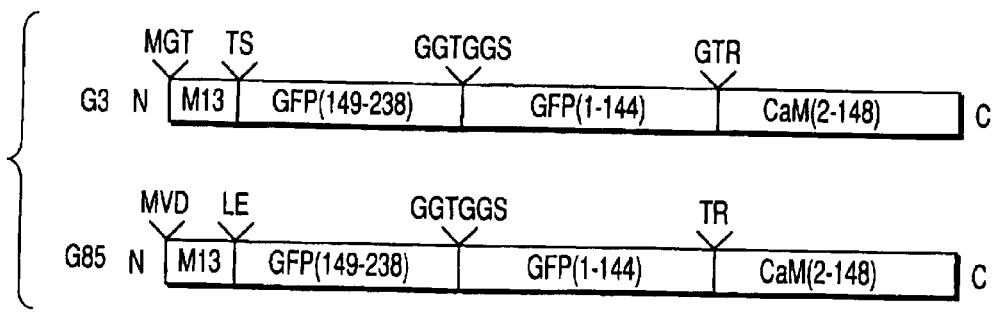
F I G. 2

METHOD OF PRODUCING A BIOSENSOR PROTEIN CAPABLE OF REGULATING A FLUORESCENCE PROPERTY OF GREEN FLUORESCENT PROTEIN, AND THE BIOSENSOR PROTEIN PRODUCED BY THE METHOD

CROSS-REFERENCE TO RELATED APPLICATIONS

This application is based upon and claims the benefit of priority from the prior Japanese Patent Application No. 2000-356047, filed Nov. 22, 2000, the entire contents of which are incorporated herein by reference.

BACKGROUND OF THE INVENTION

1. Field of the Invention

The present invention relates to a method of producing a biosensor protein capable of regulating a fluorescence property of green fluorescent protein. Furthermore, the present invention relates to a biosensor protein (hereinafter also referred to as a biosensor) produced by the above method and a biosensor gene encoding the biosensor protein. More specifically, the present invention relates to a calcium-sensing biosensor protein (hereinafter also referred to as a calcium sensor) produced by the above method and a biosensor gene encoding the calcium-sensing biosensor protein.

2. Description of the Related Art

Up to now, several biosensors have been developed by applying the fluorescence resonance energy transfer (FRET) to green fluorescent protein (hereinafter also referred to as "GFP"). Recently, it was reported that a new type of biosensor wherein a single GFP was capable of changing the fluorescence intensity without applying FRET has been developed. However, the sensitivity of the new type of biosensor was so low that it was not used in practice. To make the present invention, the present inventor has newly found that the problem of the low sensitivity was caused by insufficient examination of the linking site between GFP and a functional protein employed in the biosensor.

With respect to a calcium sensor among biosensors, roughly four types of calcium sensors have been developed. Hereinafter, outlines and shortcomings of these calcium sensors will be described.

1) A Calcium-Sensitive Synthetic Dye:

This is a chemically synthesized dye which has sensitivity to calcium, and widely used at present. The dye is loaded from the outside into a cell at the time of use. Membrane-permeable form of the dye (AM form) is easy to load into cells. However, AM form of the dye is loaded into all of the cell, so that it is difficult to introduce the dye into only a specific cell. To introduce the dye into the specific cell, the dye must be injected by the use of a glass needle or the like.

2) Aequorin:

This is a protein which reacts to calcium and emits light. Aequorin is directly injected into cells at the time of use, or an aequorin-encoding gene is incorporated into a cell before use. However, aequorin requires a coenzyme to function in a cell, so that the coenzyme must be supplied to the cell. Furthermore, the light emitted therefrom is extremely weak.

3) A Calcium-Sensitive Protein to which FRET is Applied:

This protein is composed of calcium-sensitive calmodulin (CaM), a partial sequence of myosin light chain kinase (which is bound to CaM), and two GFPs differing in fluorescence color. The protein utilizes the characteristics that the distance between two GFPs becomes shorter by a conformational change of CaM when calcium is bound to CaM, thereby inducing FRET, and as a result, the intensity of the fluorescence emitted from the two GFPs are altered. At the time of use, the protein is directly injected into cells, or the gene encoding the protein is incorporated into a cell. However, the change in the fluorescence intensity caused by the FRET is a little, and thus its signal is extremely weak. It is therefore hard to detect the signal by a conventional laser microscope equipped with an argon laser ($\lambda$=488 nm).

4) A Calcium-Sensitive Protein Composed of a Single GFP:

The calcium-sensitive protein has structure where CaM is bound between the 144th and the 146th amino acids of the amino acid sequence of GFP. The protein utilizes the characteristics that the CaM protein causes a conformational change of the GFP when calcium is bound to CaM, thereby altering the intensity of the fluorescence emitted from GFP. This protein is directly injected into a cell at the time of use, or the gene encoding the protein is introduced into a cell before use. However, since the calcium sensitivity of the protein is low, so that the signal/noise ratio becomes low in the cell in fact. This fact makes it difficult to measure a signal.

BRIEF SUMMARY OF THE INVENTION

The present invention was made with the view of overcoming the aforementioned problems. An object of the present invention is to provide a method of producing a biosensor protein capable of regulating a fluorescence property of green fluorescent protein, and to provide a biosensor protein produced by the method and a biosensor gene encoding the biosensor protein. Particularly, an object of the present invention is to provide a calcium-sensing biosensor protein produced by the method and a biosensor gene encoding the calcium-sensing biosensor protein.

More specifically, the object of the present invention is to produce a biosensor protein (particularly a calcium-sensing biosensor protein) whose sensitivity to a substance to be detected is high enough to use practically and which makes it possible to measure easily. Further object of the present invention is to produce a biosensor protein (particularly a calcium-sensing biosensor protein) which is introduced into a specific cell easily and which makes it possible to measure without a specific detection device, a coenzyme, and so on.

To attain the aforementioned objects, the present invention provides the means [1] to [19] described below.

[1] A method of producing a biosensor protein capable of regulating a fluorescence property of green fluorescent protein or its derivative by modifying the structure of green fluorescent protein or its derivative, comprising the steps of:

(A) predicting a hotspot amino acid residue affecting a fluorescence property of green fluorescent protein or its derivative;

(B) producing various fusion proteins which have the structure linked with a modified fluorescent protein and one or more functional molecules, the modified fluorescent protein being the protein obtained by cleaving amino acid sequence of green fluorescent protein or its derivative in the vicinity of the hotspot amino acid residue and modifying the structure of green fluorescent protein or its derivative, and the functional molecules each being the molecules capable of transmitting their conformational changes to the modified fluorescent protein to cause a conformational change of the modified fluorescent protein, thereby altering the fluorescence property of the modified fluorescent protein;

(C) reacting the resultant various fusion proteins with a factor affecting the conformation of any of the functional molecules; and (D) screening a fusion protein exhibiting a change in the fluorescence property by the reaction of the step (C), as a biosensor protein, from the various fusion proteins.

[2] The method described in [1], wherein the fluorescence property is fluorescence intensity.

[3] A biosensor protein comprising (1) and (2) below:
(1) a modified fluorescent protein which is obtained by cleaving amino acid sequence of green fluorescent protein or its derivative in the vicinity of a hotspot amino acid residue which affects the fluorescence property, and modifying the structure of the green fluorescent protein or its derivative; and
(2) one or more functional molecules which are capable of transmitting their conformational changes to the modified fluorescent protein to cause a conformational change of the modified fluorescent protein, thereby altering the fluorescence property of the modified fluorescent protein.

[4] The biosensor protein described in [3], wherein the fluorescence property is fluorescence intensity.

[5] The biosensor protein described in [3] or [4], wherein the hotspot amino acid residue corresponds to the 148th amino acid of amino acid sequence of green fluorescent protein.

[6] The biosensor protein described in [3] or [4], wherein the hotspot amino acid residue corresponds to the 94th amino acid of amino acid sequence of green fluorescent protein.

[7] The biosensor protein described in [3] or [4], wherein the hotspot amino acid residue corresponds to the 96th amino acid of amino acid sequence of green fluorescent protein.

[8] The biosensor protein described in [3] or [4], wherein the hotspot amino acid residue corresponds to the 222nd amino acid of amino acid sequence of green fluorescent protein.

[9] A biosensor protein comprising (1) and (2) below:
(1) a modified green fluorescent protein having the following amino acid sequences (a) and (b) in this order from the N terminus:
(a) an amino acid sequence of X-th to 238th position of green fluorescent protein; and
(b) an amino acid sequence of 1st to Y-th position of green fluorescent protein,
(where X is an arbitrary number from 148 to 150, and Y is an arbitrary number from 140 to 147); and
(2) one or more functional molecules which are capable of transmitting their conformational changes to the modified green fluorescent protein to cause a conformational change of the modified green fluorescent protein, thereby altering the fluorescence property of the modified green fluorescent protein.

[10] A biosensor protein comprising the following sequences (a) to (h) sequentially from the N terminus:
(a) an amino acid sequence containing methionine (linker X);
(b) myosin light chain kinase protein or a partial amino acid sequence thereof;
(c) an amino acid sequence (linker Y) for linking the above sequence (b) and the following sequence (d);
(d) an amino acid sequence from X-th to 238th position of green fluorescent protein (where X is an arbitrary number from 148 to 150);
(e) an amino acid sequence for linking the above sequence (d) and the following sequence (f);
(f) an amino acid sequence from 1st to Y-th position of green fluorescent protein (where Y is an arbitrary number from 140 to 147);
(g) an amino acid sequence (linker Z) for linking the above sequence (f) and the following sequence (h); and
(h) calmodulin protein or a partial amino acid sequence thereof.

[11] A biosensor protein comprising (1) and (2) below:
(1) a modified green fluorescent protein having the following amino acid sequences (a) and (b) in this order from the N terminus:
(a) the amino acid sequence from the 149th to 238th position of green fluorescent protein, and
(b) the amino acid sequence from the 1st to 144th position of green fluorescent protein; and
(2) one or more functional molecules which are capable of transmitting their conformational changes to the modified green fluorescent protein to cause a conformational change of the modified green fluorescent protein, thereby altering the fluorescence property of the modified green fluorescent protein.

[12] A biosensor protein comprising the following sequences (a) to (h) sequentially from the N terminus:
(a) an amino acid sequence containing methionine (linker X);
(b) myosin light chain kinase protein or a partial amino acid sequence thereof;
(c) an amino acid sequence (linker Y) for linking the above sequence (b) and the following sequence (d);
(d) the amino acid sequence from the 149th to 238th position of green fluorescent protein;
(e) an amino acid sequence for linking the above sequence (d) and the following sequence (f);
(f) the amino acid sequence from the 1st to 144th position of green fluorescent protein;
(g) an amino acid sequence (linker Z) for linking the above sequence (f) and the following sequence (h); and
(h) calmodulin protein or a partial amino acid sequence thereof.

[13] The biosensor protein described in any one of [3]–[9], and [11], wherein the functional molecules are calmodulin protein or a partial amino acid sequence thereof, and myosin light chain kinase protein or a partial amino acid sequence thereof.

[14] A biosensor protein comprising the following sequences (a) to (h) sequentially from the N terminus:
(a) Met-Gly-Thr or Met-Val-Asp (linker X);
(b) a partial amino acid sequence of myosin light chain kinase protein (Ser—Ser-Arg—Arg-Lys-Trp-Asn-Lys-Thr-Gly-His-Ala-Val-Arg-Ala-Ile-Gly-Arg-Leu-Ser—Ser) [SEQ ID NO:6]
(c) Leu-Glu (linker Y);
(d) the amino acid sequence from the 149th to 238th position of green fluorescent protein;
(e) Gly—Gly-Thr-Gly—Gly-Ser (linker amino acid sequence) [amino acid 117 to 122 of SEQ ID NO:8]

(f) the amino acid sequence from the 1st to 144th position of green fluorescent protein;
(g) Gly-Thr-Arg or Thr-Arg (linker Z); and
(h) the amino acid sequence from the 2nd to 148th position of rat calmodulin protein.

[15] A biosensor protein comprising the following sequences (a) to (c) in this order from the N terminus:
(a) the amino acid sequence from the 1st to 144th position of green fluorescent protein;
(b) one or more functional molecules which are capable of transmitting their conformational changes to the modified green fluorescent protein to cause a conformational change of the modified green fluorescent protein, thereby altering the fluorescence property of the modified green fluorescent protein; and
(c) the amino acid sequence from the 149th to 238th position of green fluorescent protein.

[16] The biosensor protein described in [15], wherein the functional molecules are calmodulin protein or a partial amino acid sequence thereof, and myosin light chain kinase protein or a partial amino acid sequence thereof.

[17] A biosensor protein comprising the following sequences (a) to (g) sequentially from the N terminus:
(a) the amino acid sequence from the 1st to 144th position of green fluorescent protein;
(b) an amino acid sequence (linker A) for linking the above sequence (a) and the following sequence (c);
(c) calmodulin protein or a partial amino acid sequence thereof;
(d) an amino acid sequence (linker B) for linking the above sequence (c) and the following sequence (e);
(e) myosin light chain kinase protein or a partial amino acid sequence thereof;
(f) an amino acid sequence (linker C) for linking the above sequence (e) and the following sequence (g); and
(g) the amino acid sequence from the 149th to 238th position of green fluorescent protein.

[18] A biosensor protein comprising the following sequences (a) to (g) sequentially from the N terminus:
(a) the amino acid sequence from the 1st to 144th position of green fluorescent protein;
(b) Gly-Thr-Arg (linker A);
(c) the amino acid sequence from the 2nd to 148th position of rat calmodulin protein;
(d) Gly-Thr or Gly-Thr-Gly-Ser-Gly—Gly-GlY-Ser (linker B) [SEQ ID NO:17];
(e) a partial amino acid sequence of myosin light chain kinase protein Ser—Ser-Arg—Arg-Lys-Trp-Asn-Lys-Thr-Gly-His-Ala-Val-Arg-Ala-Ile-Gly-Arg-Leu-Ser—Ser) [SEQ ID NO:6];
(f) Thr-Ser (linker C); and
(g) the amino acid sequence from the 149th to 238th position of green fluorescent protein.

[19] A biosensor gene encoding the biosensor protein described in any one of [3]–[18].

BRIEF DESCRIPTION OF THE SEVERAL VIEWS OF THE DRAWING

FIG. 1A is a schematic view showing structure of GFP;
FIG. 1B is a schematic view showing structure of a calcium sensor protein using a modified GFP;
FIG. 1C is a schematic view showing structure of a modified GFP; and
FIG. 1D is a schematic view showing structure of a calcium sensor protein using a modified GFP.

FIG. 2 shows primary structure of calcium sensor proteins (G3 and G85).

DETAILED DESCRIPTION OF THE INVENTION

Figure 3:
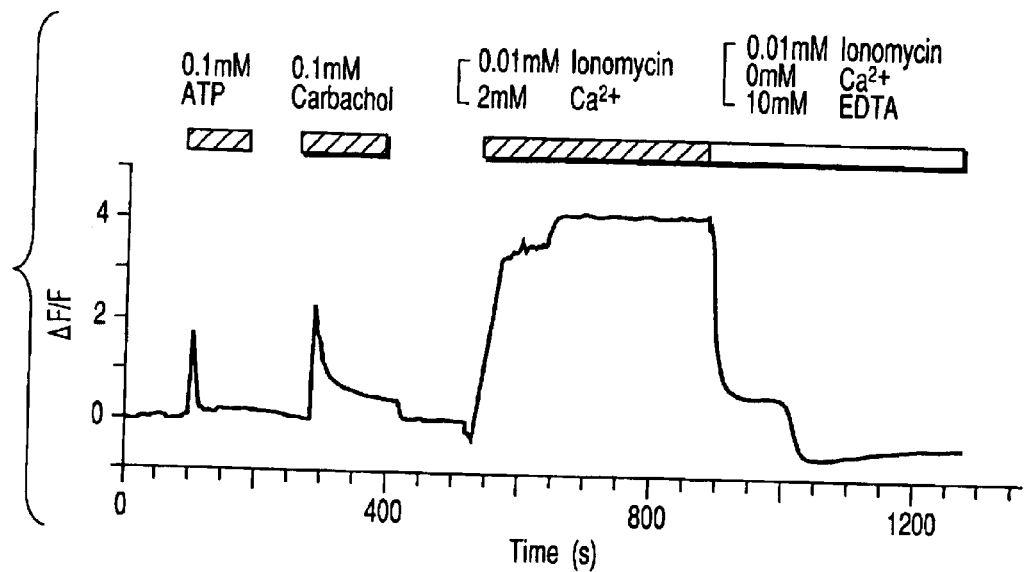
FIG. 3 shows a profile of the fluorescence intensity of a calcium sensor protein expressing in an HEK 293 cell, which changes in response to ATP and carbachol.

In the following, the method of producing a biosensor protein capable of regulating the fluorescence property of green fluorescent protein of the present invention will be explained in order of the steps (A) to (E).

The biosensor protein of the present invention is made of a single-molecular green fluorescent protein. In the present invention, the biosensor protein may be also made of a derivative of green fluorescent protein. A derivative of green fluorescent protein means any derivative of green fluorescent protein including YFP (Yellow Fluorescent Protein), CFP (Cyan Fluorescent Protein), and BFP (Blue Fluorescent Protein).

In this specification, the biosensor protein made of green fluorescent protein will be described as a representative example. Therefore, the present invention is not limited to the example.

(Method of Producing a Biosensor Protein of the Present Invention)

(A) Step of predicting a hotspot amino acid residue affecting a fluorescence property of green fluorescent protein:

Green fluorescent protein (GFP) is a protein consisting of 238 amino acids. GFP used in the present invention is a recombinant GFP (EGFP) obtained from Clontech. The EGFP contains valine (gtg) (not a constituent of original GFP) which is inserted at the back of methionine of the N terminus of original GFP. The valine is designated as "amino acid No. 1'". The valine (gtg)(amino acid No. 1') is omitted from the nucleotide sequence and amino acid sequence of the GFP in Sequence ID No: 1, for the sake of convenience. In this text, "the n-th amino acid of green fluorescent protein" or "the amino acid of n-th position of green fluorescent protein" corresponds to the position of the 1st to 238th amino acids in the amino acid sequence described in Sequence ID No: 1.

In the present invention, all biosensor proteins are actually produced using the aforementioned EGFP, which has valine (amino acid No. 1') at the back of methionine of the N terminus of GFP.

For the sake of convenience in the present invention, the structure of GFP is shown in a schematic view of FIG. 1A. GFP has a chromophore in the center of the inside of its molecular structure. GFP can be obtained by expressing a plasmid (e.g., pEGFP-N1 (Clontech)) containing GFP-encoding cDNA.

In the present invention, the "hotspot amino acid residue" affecting the fluorescence property of GFP refers to an amino acid residue of GFP which acts as an indicator of a GFP modification site, in making a modified green fluorescent protein as described later. The structure of GFP is modified in the vicinity of the above hotspot amino acid residue, and thereby it becomes possible to produce a desired modified green fluorescent protein.

"Modification of GFP structure" preferably means cleaving GFP in the vicinity of the predicted hotspot amino acid residue (preferably, at any position within amino acids before and behind the hotspot amino acid residue), and eliminating the appropriate number of amino acids (preferably 1 to 10 amino acids) from the cleavage site. However, the modification of GFP structure is not limited to the aforementioned modification, as long as it can produce a desired modified green fluorescent protein, and GFP may be modified by any modification process.

The desired modified green fluorescent protein (modified GFP) refers to a protein which is obtained by modifying the structure of GFP such that its fluorescence property can be reversibly changed, as described later. The phrase "fluorescence property can be reversibly changed" means that the conformation of the modified GFP reversibly changes by the presence or absence of a factor capable of causing a conformational change of the modified GFP (i.e., a biosensor-detecting factor), thereby altering the fluorescence property of the modified GFP in a reversible manner. Such reversible change of the fluorescence property refers to a change detectable by a fluorescence microscope, a laser microscope or the like, and preferably a change detectable with the naked eye. As an example of the change in the fluorescence property, a change in the fluorescence intensity may be employed. In this case, the abovementioned change means that $\Delta F/F$ (=change amount of fluorescence intensity/initial fluorescence intensity) is preferably at least 0.1 or more, and more preferably within the range of 1 to 10.

In the present invention, the fluorescence property refers to the property such as fluorescence intensity, fluorescence wavelength, a ratio of the fluorescence intensity, absorbance, absorption wavelength, or the like. Of these, the fluorescence intensity is used herein as the fluorescence property.

The present invention is the first to find the concept of the hotspot amino acid residue. More specifically, the present inventor produced various types of biosensor proteins having a variety of modified GFPs, and thereby he found that the amino acid residue, which has a strong effect upon the fluorescence property of GFP, was present in GFP. The finding of the above amino acid residue led to the concept of the hotspot amino acid residue.

By making various biosensor proteins having a variety of modified GFPs on an experimental basis, the position of the hotspot amino acid residue can be predicted according to the performances of the obtained biosensor proteins. Also, the position of the hotspot amino acid residue can be predicted based on the crystal structure of GFP. More specifically, there is high possibility that the hotspot amino acid residue may be an amino acid which is bound to the chromophore of GFP via hydrogen bond. Therefore, the amino acid, which is bound to the chromophore via hydrogen bond, may be predicted as the hotspot amino acid residue on the basis of the crystal structure of GFP.

In the present invention, it is predicted that the hotspot amino acid residue of GFP is an amino acid selected from the amino acids of 94th, 96th, 148th and 222nd positions of GFP. The amino acid residues of these positions are preferable as the hotspot amino acid residue, but it is not limited to these positions.

(B) Step of producing various fusion proteins which have the structure linked with a modified green fluorescent protein and one or more functional molecules, the modified green fluorescent protein being the protein obtained by cleaving amino acid sequence of green fluorescent protein in the vicinity of the hotspot amino acid residue and modifying the structure of green fluorescent protein, and the functional molecules each being the molecules capable of transmitting their conformational changes to the modified green fluorescent protein to cause a conformational change of the modified green fluorescent protein, thereby altering the fluorescence property of the modified green fluorescent protein:

In the following, this step will be explained on the assumption that the hotspot amino acid residue (predicted in the step (A)) is the n-th amino acid of GFP.

In the present invention, the modified GFP preferably means those constructed by the steps below:

cleaving original GFP in the vicinity of the hotspot amino acid residue (e.g., between the n-th amino acid and the (n+1)th amino acid of GFP);

removing the amino acids in the cleavage site (e.g., amino acids from the (n−a)th to the n-th position of GFP), thereby modifying the molecular structure of GFP; and linking the N terminus and the C terminus of original GFP with appropriate linker amino acids (e.g., Gly—Gly-Thr-Gly—Gly-Ser [amino acids 117 to 122 of SEQ ID NO:8]) in case of necessity (see FIG. 1C).

In this text, GFP (i.e., unmodified GFP) is also referred to "original GFP" in order to distinguish it from the modified GFP.

However, even if a modified GFP of a single chain is not formed by linking the N terminus and the C terminus of original GFP with the linker amino acids, two discrete GFP fragments may function in a cell, like a modified GFP of the single chain.

The linker amino acids for connecting the N terminus and C terminus of original GFP preferably have an amino acid sequence consisting of 2 to 10 amino acid molecules. The linker amino acids more preferably have an amino acid sequence rich in glycine. Particularly preferable example of the linker amino acids includes Gly—Gly-Thr-Gly—Gly-Ser [amino acids 117 to 122 of SEQ ID NO:8]. However, the linker amino acid sequence is not restricted to this example.

For example, if a modified GFP is prepared by cleaving original GFP between the n-th amino acid and the (n+1)th amino acid of GFP, removing the amino acids from the (n−a)th to the n-th position of GFP, and linking the original N-terminus and C-terminus of GFP with the linker amino acids, the modified GFP has, in this order from the N-terminus, the (n+1)th to the 238th amino acids, the linker amino acids, and the 1st to the (n−a−1)th amino acids. In a later step, a functional molecule is linked at a newly-created N-terminus and/or C-terminus of the modified GFP (see FIG. 1D).

On the other hand, when the modification is performed by cleaving original GFP between the n-th amino acid and the (n+1)th amino acid of GFP, removing the amino acids from the (n−a)th to the n-th position of GFP, and leaving the original N terminus and C terminus unlinked, the modified GFP thus obtained consists of two discrete fragments, that is, one fragment of an amino acid sequence from the 1st to the (n−a−1)th position, and the other fragment of an amino acid sequence from the (n+1)th to the 238th position. In this case, the two discrete fragments may be linked by interposing a functional molecule between them in a later step, thereby forming a single-chain protein (see FIG. 1B). Examples of such a single-chain protein are biosensor proteins listed in Table 5 below. Even if the modified GFP does not have the structure of the single-chain protein, two discrete GFP fragments may work in a cell, like a modified GFP of the single chain.

The phrase "the vicinity of the hotspot amino acid residue (the n-th amino acid residue) at which original GFP is cleaved" refers to, for example, the range of the (n+5)th to (n−5)th position, preferably the range of the (n+2)th to (n−2)th position. Furthermore, the number of amino acids to be removed (namely, the value of a+1) is, for example, 1–10, preferably 4.

The various modified GFPs satisfying the aforementioned explanation of the modified GFP may be candidates for the biosensor protein of the present invention. However, the cleavage site in the vicinity of the hotspot amino acid residue and the number of amino acids to be removed may be appropriately set by one skilled in the art. For example, the cleavage site and the number of amino acids to be removed may be varied as shown in Tables 1 and 2.

In the present invention, the functional molecule which is linked to the modified GFP is not particularly limited, as long as it is capable of causing a conformational change itself by binding a factor acting on the functional molecule (i.e., a biosensor-detecting-factor) and it is capable of transmitting the conformational change to the modified GFP. In this text, "a conformational change" means a change of stereostructure (i.e., three-dimensional structure).

Therefore, the functional molecule used herein must be linked to the modified GFP at a position which it can transmit its conformational change to the modified GFP, thereby inducing the conformational change of the modified GFP. For this reason, the functional molecule is preferably linked to the modified GFP at a position near the modified portion thereof. More specifically, the functional molecule is preferably linked to the cleavage site of original GFP via a linker molecule.

The functional molecule may consist of a single molecule, or two or more molecules. In the case where the functional molecule consists of two molecules, the factor acting on the functional molecule (i.e., biosensor-detecting-factor) first causes a conformational change in one functional molecule of the two molecules. Next, this conformational change induces a conformational change in the other functional molecule. Finally, each conformational change in two functional molecules can contribute to a conformational change of the modified GFP. Similarly in the case where the functional molecule consists of more than two molecules, the initial action of the factor on one functional molecule is transmitted to another functional molecule in turn, like signal transduction. Finally, each conformational change of all the functional molecules can act upon the modified GFP, causing a conformational change of the modified GFP.

As described above, in the case where the functional molecule consists of two or more molecules, conformational change each of the functional molecules can affect the structure of the modified GFP. Therefore, the effect of two or more functional molecules upon the modified GFP is larger than that of a single functional molecule. As a result, there is much possibility that the fluorescence property of the modified GFP may be drastically changed.

In the present invention, it is not always necessary that the functional molecule to be connected to the modified GFP has a complete structure as expressed in vivo. The functional molecule may have a partial structure which includes only a binding site of the factor acting on the functional molecule, as long as it can play the aforementioned role of functional molecule.

A preferable example of the functional molecule is a protein molecule. Specific examples of the functional molecule is a combination of calmodulin protein and myosin light chain kinase protein, and a combination of a CRE (Cyclic AMP Responsive Element) binding protein (CREB) and a CREB binding protein (CBP), but it is not limited to them.

For example, calmodulin protein and a part of myosin light chain kinase protein capable of binding to calmodulin (that is, M13 fragment) are employed as the functional molecules in the examples explained later. When these functional molecules are linked to the modified GFP to make a fusion protein, the fusion protein can function as a calcium sensor.

FIGS. 1B and 1D show schematic structure of the fusion proteins, wherein the functional molecules (i.e., calmodulin protein (CaM) and a part of myosin light chain kinase (M13)) are linked to the modified GFP. In addition, examples of primary structure of the fusion proteins are shown in FIG. 2.

As shown in FIG. 2, the modified GFP and the functional molecules are linked by linker molecules consisting of several amino acids. To distinguish individual linker molecules, the linker having an initiation codon (Met) at the N terminus of the fusion protein is designated as linker X; the linker connecting the N terminus side of the modified GFP and the functional molecule (M13) is designated as linker Y; and the linker connecting the C terminus side of the modified GFP and the functional molecule (CaM) is designated as linker Z. With respect to the linker amino acids (GGTGGS) for linking the original N terminus and C terminus of GFP, the following explanation of the modified GFP can be referred to.

These linkers are not necessarily limited in length and sequence, but preferably have a length of 0 to 10 amino acids, more preferably 2 amino acids. The linker Y preferably has a sequence of leucine-glutamic acid.

Each linker is a portion for transmitting the conformational change of the functional molecule to the modified GFP. Therefore, the degree of the conformational change of the modified GFP is significantly affected depending upon length and sequence of each linker. A choice of length and sequence of each linker must be made depending upon the type of functional molecule to be linked. However, the modified GFP and the functional molecule may be directly linked without the linker.

As a matter of fact, it is necessary to produce a variety of biosensor proteins by varying length and sequence of the linker and to evaluate the performance of the biosensor proteins in experiments.

In the present invention, more specifically, a variety of biosensor proteins are made by varying sequence of linker Y which links the modified GFP and the functional molecule (M13), and the resultant biosensor proteins are checked for their reactivity (See Tables 1 to 4).

In these biosensor proteins, when the N terminus of the modified GFP starts from the amino acid of the 149th position of original GFP, the amino acid of linker Y adjacent to the N terminal amino acid of the modified GFP is regarded as "the amino acid corresponding to the 148th position of original GFP". Furthermore, the amino acid of linker Y adjacent to "the amino acid corresponding to the 148th position of original GFP" is regarded as "the amino acid corresponding to the 147th position of original GFP".

Similarly, when the N terminus of the modified GFP starts from the amino acid of the 150th position of original GFP, the amino acid of linker Y located two amino acids away from the N terminal amino acid of the modified GFP is regarded as "the amino acid corresponding to the 148th position of original GFP".

As shown by the biosensor proteins listed on Tables 1 to 4, when "the amino acid corresponding to the 148th position of original GFP" in the amino acid sequence of linker Y has an acidic side chain (Asp of G52, Glu of G18 and G79) or a side chain having a hydroxyl group (Ser of G3 and G17, Thr of G22, Tyr of G47), the functionally reactive biosensor may be formed. Conversely, when "the amino acid corresponding to the 148th position of original GFP" has a basic side chain (Lys of G62, Arg of G19 and G75), the reactivity of the biosensor tends to be reduced.

When "the amino acid corresponding to the 148th position of original GFP" has a hydroxyl group at the side chain, the biosensor protein further exhibits a photoisomerization property. Furthermore, "the amino acid corresponding to the 147th position of original GFP" also has an effect upon the reactivity of the biosensor protein. "The amino acid corresponding to the 147th position of original GFP" has an advantageous effect upon the reactivity of the biosensor in the order of Leu>Thr>Gly. However, when "the amino acid corresponding to the 147th position of original GFP" is Pro, it has little effect on the increase in the reactivity of Arg corresponding to the 148th position (See G19). As described above, it is possible to select an appropriate linker sequence by altering the linker sequence variously.

The biosensor protein (i.e., the fusion protein) may be formed by a known genetic engineering procedure. More specifically, first, a fusion gene is made by separately preparing each gene fragment encoding each protein to be fused (that is, a gene encoding a modified GFP and a gene encoding a functional molecule) by polymerase chain reaction (PCR), and linking these fragments to each other. Then, the fusion protein is produced by introducing a plasmid comprising the above fusion gene into a desired cell and expressing the fusion gene.

(C) Step of reacting the resultant various fusion proteins with a factor affecting the conformation of any of the functional molecules:

As the factor affecting the conformation of a functional molecule constituting the fusion protein obtained in the step (B), it is possible to use a factor capable of causing the conformational change of the functional molecule directly by binding to the functional molecule. Alternatively, a molecule known to increase the intracellular level of the factor affecting the conformation of the functional molecule, may be used.

When the functional molecules are calmodulin protein and myosin light chain kinase, calcium ion may be used as the factor affecting the conformation of the functional molecules. Calcium ion can cause the conformational change of calmodulin by binding to calmodulin. Alternatively, it is possible to use a factor such as ATP, carbachol, caffeine, or thapsigargin, which is known to increase the calcium ion concentration in a cell expressing the fusion protein. By reacting the fusion protein with the above factor, the function of the fusion protein as a biosensor (calcium sensor) can be confirmed.

Alternatively, when the functional molecules are a CRE binding protein (CREB) and a CREB binding protein (CBP), cyclic AMP dependent protein kinase may be used, as the factor to confirm the function as a biosensor.

Example of the method of reacting the fusion protein with the factor affecting the conformation of the functional molecule is as follows. First, cells (e.g., HEK 293 cells) producing the fusion protein of the modified GFP/functional molecules are placed in a chamber on stage of a laser microscope. Then, the factor is added to the cells. This method is preferable because the subsequent change in the fluorescence property of the fusion protein can be observed. When ATP or carbachol is used as the factor in practice, it is appropriate to suspend the factor in a perfusion solution (HBS) and add it at a concentration of 20–300 $\mu$M.

(D) Step of screening a fusion protein exhibiting a change in the fluorescence property by the reaction of the step (C), as a biosensor protein, from the various fusion proteins:

A fusion protein exhibiting a change in the fluorescence property by reaction of the step (C) can be detected by using a fluorescence-detecting apparatus, such as a CCD camera attached to a laser microscope or a fluorescence microscope. In this manner, the protein exhibiting a change in the fluorescence property is selected as the biosensor protein. The phrase "exhibiting a change in the fluorescence property" refers to exhibiting a change which is detectable by a fluorescence microscope, a laser microscope, or the like. More preferably, it refers to exhibiting a change sufficient to be observed by the naked eye. For example, when the change of the fluorescence property is represented by the change of the fluorescence intensity, the change amount of fluorescence ($\Delta F/F$=change amount of fluorescence intensity/initial fluorescence intensity) is preferably 0.1 or more, more preferably falls within the range of 1 to 10.

The biosensor protein screened in the step (D) is in a state where its fluorescence property can be reversibly changed depending upon the presence or absence of the biosensor-detecting-factor.

The aforementioned biosensor protein, which is modified so that the fluorescence property of GFP can be reversibly changed, may be said to be in a critical state capable of changing the fluorescence property.

For example, when the fluorescence property is represented by the fluorescence intensity, the biosensor protein is in the critical state between a fluorescence-emitting state and a no-fluorescence-emitting state. In the above critical state, the biosensor protein may emit no fluorescence or emit fluorescence at a low level of intensity. Alternatively, the biosensor protein in the critical state may emit fluorescence at a high level of intensity.

The phrase "the biosensor protein emits no fluorescence" refers to the state where fluorescence cannot be detected by using an optical appliance. The phrase "the biosensor protein emits fluorescence at a low level of intensity" refers to the state where the fluorescence intensity is so low that the biosensor protein can transfer to a level of high fluorescence intensity by the action of the biosensor-detecting-factor, showing the above change amount (i.e., $\Delta F/F>0.1$ or more). Similarly, the phrase "the biosensor protein emits fluorescence at a high level of intensity" refers to the state where the fluorescence intensity is so high that the biosensor protein can transfer to a level of low fluorescence intensity by the action of the biosensor-detecting-factor, showing the above change amount (i.e., $\Delta F/F>0.1$ or more).

When the biosensor protein is in a critical state and emits fluorescence at a high level of intensity, the biosensor protein can transfer to a no-fluorescence-emitting state or weak fluorescence-emitting state by a small conformational change thereof. Therefore, it may be said that the critical state is "the state where strong fluorescence can be barely emitted". Further, when the biosensor protein is in a critical state and emits no fluorescence, the biosensor protein can transfer to a fluorescence-emitting state by a small conformational change thereof. Therefore, it may be said that the critical state is "the state where fluorescence cannot be barely emitted". Similarly, when the biosensor protein is in a critical state and emits fluorescence at a low level of intensity, the biosensor protein can transfer to a strong fluorescence-emitting state by a small conformational change thereof. Therefore, it may be also said that the critical state is "the state where weak fluorescence can be barely emitted".

As described above, the biosensor protein of the present invention is in a critical state. This is because the biosensor protein in a critical state can sensitively respond to the presence or absence of the sensor-detecting-factor to cause a reversible change of the conformation thereof, thereby changing the fluorescence property reversibly (e.g., moving back and forth between a fluorescence-emitting state and a no-fluorescence-emitting state reversibly). Therefore, when the biosensor protein is in the above critical state, it can be said that it is in a state where it can function as a biosensor.

(Biosensor Protein and Biosensor Gene)

The biosensor protein of the present invention refers to that screened by the aforementioned method of producing a biosensor protein. Also, the biosensor gene of the present invention refers to the gene encoding the biosensor protein of the present invention, and is used to express the biosensor protein in a cell.

The biosensor protein of the present invention is characterized by comprising (1) and (2) below:
(1) a modified GFP, which is obtained by cleaving amino acid sequence of GFP in the vicinity of a hotspot amino acid residue which affects the fluorescence property, and modifying the structure of the GFP; and
(2) one or more functional molecules, which are capable of transmitting their conformational changes to the modified GFP to cause a conformational change of the modified GFP, thereby altering the fluorescence property of the modified GFP.

The modified GFP, which is a constituent of the biosensor protein, is as defined above. The modified GFP is preferably formed by cleaving amino acid sequence of GFP in the vicinity of the hotspot amino acid residue, and eliminating some amino acids from the cleavage site, thereby modifying the molecular structure of GFP, and if necessary, linking the original N terminus and C terminus of GFP with an appropriate amino acid sequence.

The functional molecule, which is a constituent of the biosensor protein, is also as defined above. The functional molecule is a molecule capable of causing a conformational change itself by binding a factor acting upon the functional molecule (i.e., biosensor-detecting-factor), and transmitting its conformational change to the modified GFP.

The modified GFP and the functional molecule are not particularly limited, as long as they satisfy the aforementioned definitions.

As described above, in the biosensor protein of the present invention, the functional molecule must be linked to the modified GFP at a position where the functional molecule can transmit its conformational change to the modified GFP and cause a conformational change of the modified GFP. Therefore, it is preferable that the functional molecule is linked to the modified GFP in the vicinity of the modified portion of the modified GFP. More specifically, the functional molecule is preferably linked to the cleavage site of GFP via a linker molecule.

To work as the biosensor protein of the present invention, the biosensor protein is required to reversibly change its fluorescence property depending on the presence or absence of the biosensor-detecting-factor. As an example of the fluorescence property, the fluorescence intensity is used in the present invention. As described above, the biosensor protein of the present invention is in a critical state between a fluorescence-emitting state and a no-fluorescence-emitting state, and can reversibly change its fluorescence property.

In the biosensor protein of the present invention, the hotspot amino acid residue is preferably the amino acid residue of the 148th, 94th, 96th or 222nd position of GFP.

The biosensor protein, which is employed the amino acid of the 148th position of GFP as the hotspot amino acid residue, is characterized by comprising the following (1) and (2):
(1) a modified green fluorescent protein having the following amino acid sequences (a) and (b) in this order from the N terminus:
   (a) an amino acid sequence of X-th to 238th position of green fluorescent protein, and
   (b) an amino acid sequence of 1st to Y-th position of green fluorescent protein,
      (where X is an arbitrary number from 148 to 150, and Y is an arbitrary number from 140 to 147); and
(2) one or more functional molecules, which are capable of transmitting their conformational changes to the modified green fluorescent protein to cause a conformational change of the modified green fluorescent protein, thereby altering the fluorescence property of the modified green fluorescent protein.

More specifically, the biosensor protein, which is employed the amino acid of the 148th position of GFP as the hotspot amino acid residue, is characterized by comprising the following sequences (a) to (h) sequentially from the N terminus:
(a) an amino acid sequence containing methionine (linker X);
(b) myosin light chain kinase protein or a partial amino acid sequence thereof;
(c) an amino acid sequence (linker Y) for linking the above sequence (b) and the following sequence (d);
(d) an amino acid sequence from X-th to 238th position of green fluorescent protein (where X is an arbitrary number from 148 to 150);
(e) an amino acid sequence for linking the above sequence (d) and the following sequence (f);
(f) an amino acid sequence from 1st to Y-th position of green fluorescent protein (where Y is an arbitrary number from 140 to 147);
(g) an amino acid sequence (linker Z) for linking the above sequence (f) and the following sequence (h); and
(h) calmodulin protein or a partial amino acid sequence thereof.

The linker X of sequence (a) is an arbitrary amino acid sequence containing methionine, preferably an amino acid sequence consisting of 1–10 amino acids. The linker X is more preferably the sequence of Met-Xaa—Xaa, wherein Xaa represents an arbitrary amino acid, and further preferably, the sequence of Met-Gly-Thr or Met-Val-Asp.

The linker Y of sequence (c) is an arbitrary amino acid sequence, preferably an amino acid sequence consisting of 0–10 amino acids. More preferably, in the amino acid sequence of the linker Y, "the amino acid corresponding to the 147th position of GFP" is Leu, Thr, or Gly, and "the amino acid corresponding to the 148th position of GFP" is an amino acid having an acidic side chain or a side chain with a hydroxyl group therein. Further preferably, the linker Y is the sequence of Leu-Glu.

The linker of sequence (e) is preferably an amino acid sequence consisting of 2–10 amino acids. The linker of sequence (e) is more preferably an amino acid sequence rich in an amino acid (e.g., glycine) which allows a main chain of a peptide to move with a large degree of freedom, rendering the main chain flexible. Further preferably, the linker of sequence (e) is the sequence of Gly—Gly-Thr-Gly-Gly-Ser [amino acids 117 to 122 of SEQ ID NO:8].

The linker Z of sequence (g) is an arbitrary amino acid sequence, preferably an amino acid sequence consisting of 0–10 amino acids. The linker Z is more preferably an amino acid sequence consisting of 2–3 amino acids, and further preferably the sequence of Thr-Arg.

In the following, Tables 1 and 2 list examples of the various biosensor proteins using the amino acid of the 148th position of GFP as the hotspot amino acid residue. Myosin light chain kinase (M13) and calmodulin (CaM) are used herein as the functional molecules.

molecule, is represented by Sequence ID No: 3. The nucleotide sequence encoding the M13 fragment is obtained by modifying the nucleotide sequence encoding M13 fragment of chicken (Guerriero, V et al., Biochemistry 25, 8372–8381 (1986)).

In Tables 1 and 2, the names of probe No. are given to a variety of biosensor proteins listed therein. For example, the one-dimensional structure of the probe No. G3 (hereinafter, also referred to as "G3") is shown in FIG. 2. The G3 has, in this order from the N terminus,

TABLE 1

| Probe No | Linker X | M13 | Linker Y | cpEGFP | Linker Z | CaM | Fluorescence | ATP response (Δ F/F) | Photoisomerization |
|---|---|---|---|---|---|---|---|---|---|
| G3 | MGT | ○ | TS | 149-144 | GTR | ○ | + | 0.6 | + |
| G4 | MGT | ○ | TS | 149-144 | GTR | CN | + | 1.6 | + |
| G6 | MGT | ○ | TS | 148-144 | GTR | ○ | − | nt | nt |
| G7 | MGT | ○ | TS | 147-144 | GTR | ○ | + | 0 | − |
| G8 | MGT | ○ | TS | 146-144 | GTR | ○ | + | 0 | − |
| G9 | MGT | ○ | TS | 151-144 | GTR | ○ | + | 0 | − |
| G10 | MGT | ○ | TS | 153-144 | GTR | ○ | * | nt | − |
| G11 | MGT | ○ | TS | 155-144 | GTR | ○ | * | nt | − |
| G12 | MGT | ○ | TS | 149-140 | GTR | ○ | + | 0 | + |
| G13 | MGT | ○ | TS | 148-140 | GTR | ○ | + | 0.2 | + |
| G14 | MGT | ○ | TS | 147-140 | GTR | ○ | * | nt | nt |
| G15 | MGT | ○ | TS | 146-140 | GTR | ○ | * | nt | nt |
| G16 | MGT | ○ | TS | 145-140 | GTR | ○ | * | nt | nt |

TABLE 2

(Continuation of Table 1)

| Probe No | Linker X | M13 | Linker Y | cpEGFP | Linker Z | CaM | Fluorescence | ATP response (Δ F/F) | Photoisomerization |
|---|---|---|---|---|---|---|---|---|---|
| G22 | MGT | ○ | TS | 150-144 | GTR | ○ | + | 0.6 | + |
| G23 | MGT | ○ | TS | 149-147 | GTR | CN | + | 0.2 | + |
| G24 | MGT | ○ | TS | 149-146 | GTR | CN | * | nt | nt |
| G25 | MGT | ○ | TS | 149-145 | GTR | CN | * | nt | nt |
| G27 | MGT | ○ | TS | 150-147 | GTR | CN | + | 1.0 | + |
| G28 | MGT | ○ | TS | 151-147 | GTR | CN | − | nt | nt |
| G29 | MGT | ○ | TS | 153-147 | GTR | CN | − | nt | nt |
| G30 | MGT | ○ | TS | 155-147 | GTR | CN | − | nt | nt |

The biosensor proteins listed on Tables 1 and 2 have the following amino acid sequences in this order from the N terminus:
an amino acid sequence containing methionine (linker X);
a partial amino acid sequence of myosin light chain kinase protein (M13);
a linker amino acid sequence (linker Y);
a modified GFP (cpEGFP);
a linker amino acid sequence (linker Z); and
an amino acid sequence from the 2nd to 148th position of calmodulin protein (CaM).

The amino acid sequence of rat calmodulin used herein as a functional molecule is represented by Sequence ID No:4. Each amino acid from the 1st to 148th position of the amino acid sequence represented by Sequence ID No:4 corresponds to the "n-tb amino acid of calmodulin protein" described in this text. In the amino acid sequence represented by Sequence ID No:4, methionine of the N terminus is omitted therefrom. This is the reason why methionine of the N terminus is cleaved out by post-translational modification, after translation of genetic code of calmodulin into amino acids.

Also, the partial amino acid sequence (M13) of myosin light chain kinase protein, which is used as a functional linker X (Met-Gly-Thr);
a partial amino acid sequence of myosin light chain kinase (Ser—Ser-Arg—Arg-Lys-Trp-Asn-Lys-Thr-Gly-His-Ala-Val-Arg-Ala-Ile-Gly-Arg-Leu-Ser—Ser) [SEQ ID NO:6];
linker Y (Thr-Ser);
the modified GFP (the amino acid sequence of the 149-238th position of GFP, the linker amino acids (Gly—Gly-Thr-Gly—Gly-Ser) [amino acids 117 to 122 of SEQ ID NO:8], and the amino acid sequence of the 1-144th position of GEP, in this order from the N terminus);
linker Z (Gly-Thr-Arg); and
the amino acid sequence of the 2nd to 148th position of rat calmodulin.

In Tables 1 and 2, the amino acid sequences in each column of Linkers X, Y and Z are represented by single-letter notation. The symbol "O" in the column of M13 refers to the sequence of (Ser—Ser-Arg—Arg-Lys-Trp-Asn-Lys-Thr-Gly-His-Ala-Val-Arg-Ala-Ile-Gly-Arg-Leu-Ser—Ser) [SEQ ID NO:8]. The number "149-144" in the column of cpEGFP means that the modified GFP has, in this order from the N terminus, the amino acid sequence of the 149-238th position of GFP, the linker amino acids (Gly—Gly-Thr-Gly-Gly-Ser) [amino acids 117 to 122 of SEQ ID NO:8], and the amino acid sequence of the 1-144th position of GFP. The symbol "O" in the column of CaM represents the amino acid sequence of the 2nd to 148th position of original rat calmodulin, and the symbol "CN" represents the amino acid sequence of the 2nd to 148th position of calmodulin mutant CaMCN (Persechini A et al., 1997, Cell Calcium 22, 209-216). The symbol "+" in the column ofFluorescence means that a biosensor protein emits weak fluorescence before ATP is added, whereas the symbol "−" means that a biosensor protein emits no fluorescence before ATP is added. Further, the symbol "*" represents that a biosensor protein emits weak fluorescence at a high intracellular calcium concentration of about 2 mM. The value "ΔF/F" in the column of ATP response is a value (arbitrary unit) obtained by dividing "ΔF" by "F", wherein "ΔF" is a change amount of fluorescence intensity between before and after addition of ATP and "F" is a fluorescence intensity before addition of ATP, in the cell (HEK cell) producing a biosensor protein. The symbol "nt" represents "not tested". The symbol "+" in the column of Photoisomerization means that a biosensor protein causes photoisomerization, and the symbol "−" means that a biosensor protein causes no photoisomerization.

As shown in Tables 1 and 2, a variety of biosensor proteins are produced by varying the N terminus of cpEGFP within the amino acids of the 145-155th positions and varying the C terminus of cpEGFP within the amino acids of the 140-147th positions. The resultant biosensor proteins are checked for reactivity to ATP. As a result, the biosensor proteins having the N terminus starting from the amino acid of the 149 or 150th position, exhibit a high reactivity to ATP. The biosensor proteins having the C terminus terminating at the amino acid of 140, 144, or 147th position, exhibit a reactivity to ATP.

In some cases, it may be considered that the amino acid of the 148th position is included in linker Y. More specifically, when the N terminus of the modified GFP starts from the amino acid of the 149th position of original GFP, the amino acid of linker Y adjacent to the N terminal amino acid of the modified GFP may be regarded as "the amino acid corresponding to the 148th position of original GFP". Similarly, when the N terminus of the modified GFP starts from the amino acid of the 150th position of original GFP, the amino acid of linker Y located two amino acids away from the N terminal amino acid of the modified GFP may be regarded as "the amino acid corresponding to the 148th position of original GFP".

More preferably, the biosensor protein employing the amino acid of the 148th position of GFP as the hotspot amino acid residue is characterized by comprising the following (1) and (2):

(1) a modified green fluorescent protein having the following amino acid sequences (a) and (b) in this order from the N terminus:
  (a) the amino acid sequence from the 149th to 238th position of green fluorescent protein, and
  (b) the amino acid sequence from the 1st to 144th position of green fluorescent protein; and (2) one or more functional molecules, which are capable of transmitting their conformational changes to the modified green fluorescent protein to cause a conformational change of the modified green fluorescent protein, thereby altering the fluorescence property of the modified green fluorescent protein.

More specific example of the above more preferable biosensor protein is characterized by comprising the following sequences (a) to (h) sequentially from the N terminus:

(a) an amino acid sequence containing methionine (linker X);

(b) myosin light chain kinase protein or a partial amino acid sequence thereof;

(c) an amino acid sequence (linker Y) for linking the above sequence (b) and the following sequence (d);

(d) the amino acid sequence from the 149th to 238th position of green fluorescent protein;

(e) an amino acid sequence for linking the above sequence (d) and the following sequence (f);

(f) the amino acid sequence from the 1st to 144th position of green fluorescent protein;

(g) an amino acid sequence (linker Z) for linking the above sequence (f) and the following sequence (h); and (h) calmodulin protein or a partial amino acid sequence thereof.

The linker X of sequence (a) is an arbitrary amino acid sequence containing methionine, preferably an amino acid sequence consisting of 1–10 amino acids. The linker X is more preferably the sequence of Met-Xaa—Xaa, wherein Xaa is an arbitrary amino acid, and further preferably, the sequence of Met-Gly-Thr or Met-Val-Asp.

The linker Y of sequence (c) is an arbitrary amino acid sequence, preferably an amino acid sequence consisting of 0–10 amino acids. More preferably, the linker Y is an amino acid sequence consisting of 2 amino acids: one is "the amino acid corresponding to the 147th position of GFP", which is Leu, Thr, or Gly; and the other is "the amino acid corresponding to the 148th position of GFP", which is an amino acid having an acidic side chain or a side chain with a hydroxyl group therein. Further preferably, the linker Y is the sequence of Leu-Glu.

The linker of sequence (e) is preferably an amino acid sequence consisting of 2–10 amino acids. The linker of sequence (e) is more preferably an amino acid rich in an amino acid, such as glycine, which allows a main chain of a peptide to move with a large degree of freedom, render the main chain flexible. Further preferably, the linker sequence (e) is the sequence of Gly—Gly-Thr-Gly—Gly—Gly-Ser (amino acids 117 to 122 of SEQ ID NO: 8).

The linker Z of sequence (g) is an arbitrary amino acid sequence, preferably an amino acid sequence consisting of 0–10 amino acids. The linker Z is more preferably an amino acid sequence consisting of 2–3 amino acids, and further preferably the sequence of Thr-Arg.

Various examples of the above more preferable biosensor proteins are listed in Tables 3 and 4 in the following. Myosin light chain kinase (M13) and calmodulin (CaM) are used herein as the functional molecules.

TABLE 3

| Probe No | Linker X | M13 | Linker Y | cpEGFP | Linker Z | CaM | ATP response (Δ F/F) | n | Photoisomerization |
|---|---|---|---|---|---|---|---|---|---|
| G3 | MGT | ○ | TS | 149-144 | GTR | ○ | 0.7 | 28 | +++ |
| G17 | MGT | ○ | GS | 149-144 | GTR | ○ | 0.3 | 11 | +++ |
| G18 | MGT | ○ | LE | 149-144 | GTR | ○ | 1.6 | 78 | − |

TABLE 3-continued

| Probe No | Linker X | M13 | Linker Y | cpEGFP | Linker Z | CaM | ATP response (Δ F/F) | n | Photoisomerization |
|---|---|---|---|---|---|---|---|---|---|
| G19 | MGT | ○ | PR | 149-144 | GTR | ○ | 0 | 12 | – |
| G41 | MGT | ○ | TI | 149-144 | GTR | ○ | 0 | 18 | – |
| G44 | MGT | ○ | TP | 149-144 | GTR | ○ | 0 | 21 | – |
| G46 | MGT | ○ | TA | 149-144 | GTR | ○ | 0 | 12 | – |
| G47 | MGT | ○ | TY | 149-144 | GTR | ○ | 0.7 | 19 | ++ |
| G49 | MGT | ○ | TQ | 149-144 | GTR | ○ | 0 | 18 | – |
| G50 | MGT | ○ | TN | 149-144 | GTR | ○ | 0 | 18 | – |
| G52 | MGT | ○ | TD | 149-144 | GTR | ○ | 0.3 | 20 | – |
| G54 | MGT | ○ | TC | 149-144 | GTR | ○ | 0.3 | 21 | – |
| G55 | MGT | ○ | TW | 149-144 | GTR | ○ | 0 | 20 | – |
| G56 | MGT | ○ | TG | 149-144 | GTR | ○ | 0 | 20 | – |
| G58 | MGT | ○ | TV | 149-144 | GTR | ○ | 0 | 23 | – |

TABLE 4

(Continuation of Table 3)

| Probe No | Linker X | M13 | Linker Y | cpEGFP | Linker Z | CaM | ATP response (Δ F/F) | n | Photoisomerization |
|---|---|---|---|---|---|---|---|---|---|
| G61 | MGT | ○ | TF | 149-144 | GTR | ○ | 0.5 | 22 | – |
| G62 | MGT | ○ | TK | 149-144 | GTR | ○ | 0 | 28 | – |
| G72 | MGT | ○ | LE | 149-144 | TR | ○ | 1.6 | 67 | – |
| G75 | MGT | ○ | TR | 149-144 | GTR | ○ | 0 | 29 | – |
| G76 | MGT | ○ | TM | 149-144 | GTR | ○ | 0.6 | 23 | – |
| G77 | MGT | ○ | TT | 149-144 | GTR | ○ | 0.1 | 10 | +++ |
| G79 | MGT | ○ | TE | 149-144 | GTR | ○ | 0.5 | 26 | – |
| G80 | MGT | ○ | TH | 149-144 | GTR | ○ | 0.3 | 23 | + |
| G81 | MGT | ○ | TL | 149-144 | GTR | ○ | 0.6 | 8 | – |
| G85 | MVD | ○ | LE | 149-144 | TR | ○ | 1.5 | 16 | – |
| G22 | MGT | ○ | TS | 150-144 | GTR | ○ | 0.6 | 26 | +++ |

The biosensor proteins listed on Tables 3 and 4 have, in this order from the N terminus, an amino acid sequence containing methionine (linker X);
a partial amino acid sequence of myosin light chain kinase protein (M13);
a variety of linker amino acid sequence (linker Y);
a modified GFP (cpEGFP);
a linker amino acid sequence (linker Z); and
the amino acid sequence (CaM) of the 2nd to 148th position of calmodulin protein.

In Tables 3 and 4, the names of probe No. are given to various biosensor proteins listed therein. For example, the one-dimensional structure of the probe No. G85 (hereinafter, also referred to as "G85") is shown in FIG. 2. The G85 has, in this order from the N terminus, linker X (Met-Val-Asp);
a partial amino acid sequence of myosin light chain kinase (Ser—Ser-Arg—Arg-Lys-Trp-Asn-Lys-Thr-Gly-His-Ala-Val-Arg-Ala-Ile-Gly-Arg-Leu-Ser—Ser); [SEQ ID NO:6];
linker Y (Leu-Glu);
the modified GFP (the amino acid sequence of the 149-238th position of GFP, the linker amino acids (Gly—Gly-Thr-Gly-Gly-Ser) [amino acids 117 to 122 of SEQ ID NO:8], and the amino acid sequence of the 1-144th position of GFP, in this order from the N terminus);
linker Z (Thr-Arg); and
the amino acid sequence of the 2nd to 148th position of rat calmodulin.

In Tables 3 and 4, the amino acid sequences of the linkers X, Y and Z are represented by single-letter notation. The symbol "O" in the column of M13 represents the sequence of (Ser—Ser-Arg—Arg-Lys-Trp-Asn-Lys-Thr-Gly-His-Ala-Val-Arg-Ala-Ile-Gly-Arg-Leu-Ser—Ser); [SEQ ID NO:6]. The number "149-144" in the column of cpEGFP means that the modified GFP has, in this order from the N terminus, the amino acid sequence from the 149-238th position of GEP, the linker amino acids (Gly—Gly-Thr-Gly-Gly-Ser) [amino acids 117 to 122 of SEQ ID NO:8], and the amino acid sequence of the 1-144th position of GFP. The symbol "O" in the column of CaM represents the amino acid sequence of the 2nd to 148th position of rat-inherent calmodulin. The value "ΔF/F" in the column of ATP response is a value (arbitrary unit) obtained by dividing "ΔF" by "F", wherein ΔF is a change amount of fluorescence intensity between before and after addition of ATP and "F" is a fluorescence intensity before addition of ATP, in the cell (HEK cell) producing a biosensor protein. The column "n" refers to the number of cells tested. The symbol "+" in the column of Photoisomerization means that a biosensor protein causes photoisomerization, whereas the symbol "-" means that a biosensor protein causes no photoisomerization.

In Tables 3 and 4, the reactivity of various biosensor proteins to ATP are checked by principally varying the amino acid sequence of linkers X, Y, and Z. Biosensor proteins having the sequence of Leu-Glu as linker Y show the highest reactivity. In both cases where the sequence of linker Z is (Gly-Thr-Arg) and (Thr-Arg), there is no significant difference between them with respect to the reactivity to ATP. Furthermore, in both cases where the sequence of linker X is (Met-Gly-Thr) and (Met-Val-Asp), there is no significant difference between them with respect to the reactivity to ATP. Although the total number of the amino acids of cpEGFP (150-144) in the biosensor protein G22 is smaller than that of cpEGFP (149-144) in G3 by one, there is no significant difference between them in the reactivity.

As shown in the results of Tables 3 and 4, the biosensor proteins G18, G72, and G85 exhibit the very high reactivity, and show the value 1.5–1.6 in the change amount (ΔF/F) of fluorescence to ATP. All of the biosensor proteins G18, G72, and G85 have the modified GFPs having the N terminus starting from the 149th amino acid of original GFP, and have glutamic acid (Glu) as "the amino acid corresponding to the 148th position of GFP" in linker Y. In addition, the results show that the biosensor protein G22 exhibits a relatively low reactivity (ΔF/F=0.6), but has a sufficient sensitivity to calcium. The biosensor protein G22 has the modified GFP having the N terminus starting from the 150th amino acid of original GFP, and has threonine as "the amino acid corresponding to the 148th position of GFP" in linker Y.

From the results of Tables 3 and 4, the following facts are also demonstrated. When "the amino acid corresponding to the 148th position of GFP" in linker Y has a side chain with a hydroxyl group, such biosensor protein causes photoisomerization. This suggests that the amino acid of linker Y adjacent to the modified GFP (i.e., "the amino acid corresponding to the 148th position of GFP") is closely related to the fluorescence intensity of the biosensor protein.

Other than the biosensor proteins described in Tables 1–4, another examples of biosensor proteins are listed on Table 5. The biosensor proteins listed on Table 5 are prepared by cleaving GFP in the vicinity of the amino acid residue of the 148th position of GFP (which is the hotspot amino acid residue), and linking the functional molecules between the cleaved sites.

biosensor protein emits weak fluorescence before addition of ATP. The value "ΔF/F" in the column of ATP response is a value (arbitrary unit) obtained by dividing "ΔF" by "F", wherein "ΔF" is a change amount of fluorescence intensity between before and after addition of ATP and "F" is a fluorescence intensity before addition of ATP, in the cell (HEK cell) producing a biosensor protein. The symbol "*" in the column of ATP response represents that the biosensor protein responds to carbachol in the case of using carbachol instead of ATP. The symbol "+" in the column of Photoisomerization means that a biosensor protein causes photoisomerization.

Table 5 shows the ATP reactivity of a biosensor group having the original N terminus and original C terminus of GFP. The biosensor group reacts to ATP, but the reactivity is low. The biosensor protein A2 having a longer linker B shows higher reactivity than A1. The reactivity of this biosensor group will be improved by examining the various sequences with respect to linkers A, B and C, and a biosensor protein having higher reactivity will be produced.

The results of Tables 1 to 5 reveal that GFP has the amino acid residue of the 148th position as the hotspot amino acid residue which has a strong effect upon the fluorescence intensity of GFP. This makes it possible to control the fluorescence intensity of GFP efficiently by way of the hotspot amino acid residue. Similarly, it is predicted from the crystalline structure of GFP that a biosensor protein capable of controlling the fluorescence intensity of GFP can be constructed, if the 94th, 96th, or 222nd amino acid residue is employed as the hotspot amino acid residue, as well as the 148th amino acid residue.

Examples of the biosensor proteins of the present invention include the biosensor proteins having calmodulin pro-

TABLE 5

| Probe No. | N-terminal sequence of modified GFP | Linker A | CaM | Linker B | M13 | Linker C | C-terminal sequence of modified GFP | Fluorescence | ATP response (Δ F/F) | Photoisomerization |
|---|---|---|---|---|---|---|---|---|---|---|
| A1 | 1–144 | GTR | ○ | CT | ○ | TS | 149-238 | + | 0.3* | + |
| A2 | 1–144 | GTR | ○ | GTGSGGGS | ○ | TS | 149-238 | + | 0.5 | + |

The biosensor proteins listed on Table 5 have the following sequences in this order from the N terminus:
  the amino acid sequence of the 1st to 144th position of green fluorescent protein;
  linker A;
  a partial amino acid sequence (M13) of myosin light chain kinase;
  linker B;
  the amino acid sequence (CaM) of the 2nd to 148th position of rat calmodulin;
  linker C;
  the amino acid sequence of the 149 to 238th position of GFP.

In Table 5, the amino acid sequences of the linkers A, B and C are represented by single-letter notation. The symbol "O" in the column of M13 represents the sequence of (Ser—Ser-Arg—Arg-Lys-Trp-Asn-Lys-Thr-Gly-His-Ala-Val-Arg-Ala-Ile-Gly-Arg-Leu-Ser—Ser). The symbol "O" in the column of CaM represents the amino acid sequence of the 2nd to 148th position of rat-inherent calmodulin. The symbol "+" in the column of Fluorescence means that a tein (or a part thereof) and myosin light chain kinase (or a part thereof) as the functional molecules, as described above. However, the biosensor proteins of the present invention are not limited to them. In other words, the biosensor proteins of the present invention are not limited to those working as the aforementioned calcium sensor.

Particularly preferable example of the calcium sensor protein of the present invention is characterized by comprising the following sequences (a) to (h), sequentially from the N terminus,
  (a) Met-Gly-Thr or Met-Val-Asp (linker X);
  (b) a partial amino acid sequence of myosin light chain kinase protein (Ser—Ser-Arg—Arg-Lys-Trp-Asn-Lys-Thr-Gly-His-Ala-Val-Arg-Ala-Ile-Gly-Arg-Leu-Ser—Ser); [SEQ ID NO:6];
  (c) Leu-Glu (linker Y);
  (d) the amino acid sequence of the 149th to 238th position of green fluorescent protein;
  (e) Gly—Gly-Thr-Gly—Gly-Ser [amino acids 117 to 122 of SEQ ID NO:8];
  (f) the amino acid sequence of the 1st to 144th position of green fluorescent protein;

(g) Gly-Thr-Arg or Thr-Arg (linker Z); and (h) the amino acid sequence from the 2nd to 148th position of rat calmodulin protein.

The calcium sensor prepared in the present invention can be used when calcium concentration is measured inside or outside cells.

For example, calcium concentration can be measured by previously preparing a calcium sensor protein of the present invention by introducing a gene encoding the calcium sensor protein into E. coli or the like, and then mixing the resultant calcium sensor protein with a specimen. Further, the intracellular calcium concentration may be measured by injecting directly the calcium sensor protein produced by using E. coli or the like into a desired cell to be measured for calcium concentration. Alternatively, the intracellular calcium concentration may be measured by introducing the calcium sensor gene into the desired cell to be measured for calcium concentration, and expressing the gene in the cell.

The measurement of calcium concentration can be performed by irradiating light at a specific wavelength (e.g., excitation light at 488 nm) to a calcium sensor protein and detecting the property of the fluorescence emitted from the calcium sensor protein by means of an optical appliance (e.g., laser microscope). As regards the calcium sensor protein used for measurement, it is necessary to previously check the relationship between a known calcium concentration and the fluorescence property of the calcium sensor protein under the known calcium concentration. More specifically, for example, it is necessary to make a large amount of the calcium sensor protein by using E. coli, and previously measure the property of fluorescence wavelength and the change of fluorescence intensity in response to various calcium concentration by fluorescent spectrophotometer (See FIG. 5). The biosensor protein of the present invention has almost the same property of fluorescence wavelength as that of EGFP (Clontech). Specifically, the biosensor protein of the present invention has a maximum excitation wavelength of 489 nm and a maximum emission wavelength of 509 nm.

In the present invention, the biosensor gene refers to a gene encoding the biosensor protein of the present invention. The biosensor gene is prepared, in the form of a fusion gene, by making each gene fragment encoding individual constitutional parts (e.g., parts of a modified GFP and a functional molecule) of a biosensor protein by means of PCR, and linking the resultant each gene fragment. The biosensor gene thus prepared is introduced into an appropriate vector (pEGFP-N1, Clontech), and then the recombinant plasmid is further introduced into a cell. In this manner, the desired biosensor protein can be produced in an arbitrary cell.

(Confirmation of the Performance of the Biosensor Protein of the Present Invention)

The biosensor protein of the present invention is required checking experimentally for the performance as a sensor in advance.

The calcium sensor which was actually developed in the present invention was checked for the performance, by introducing the gene of the calcium sensor into cultured human embryonic kidney (HEK) 293 cells or mouse skeletal muscle primary cultured cells.

The calcium sensor of probe No. G85 is made by expressing the gene of the calcium sensor in the HEK 293 cells, and then a factor known to increase the calcium ion concentration in cells, such as ATP (0.1 mM) or carbachol (CCH) (0.1 mM), is added to the HEK 293 cells. The reaction profile of the calcium sensor G85 is shown in FIG. 3. The nucleotide sequence of the G85 is represented by Sequence ID No:7.

As shown in FIG. 3, the change amount ($\Delta F/F$) of fluorescence in response to ATP in the HEK 293 cells comes up to about 1.6. Such change amount can be captured by both fluorescence microscopy and naked eye. The change amount ($\Delta F/F$) of fluorescence in response to carbachol reaches about 2.2. Furthermore, it is observed that the fluorescence intensity of the calcium sensor reaches a maximum, when ionomycin (0.01 mM) and a calcium ion (2 mM) are added to increase the calcium concentration in the cells. Conversely, it is observed that the fluorescence intensity of the calcium sensor reaches a minimum, when the calcium concentration in the cells is approximated to zero by adding ionomycin (0.01 mM) and EDTA (Ethylenediamine-N,N,N',N'tetraacetic acid disodium salt)(10 mM), without adding a calcium ion.

Figure 4:
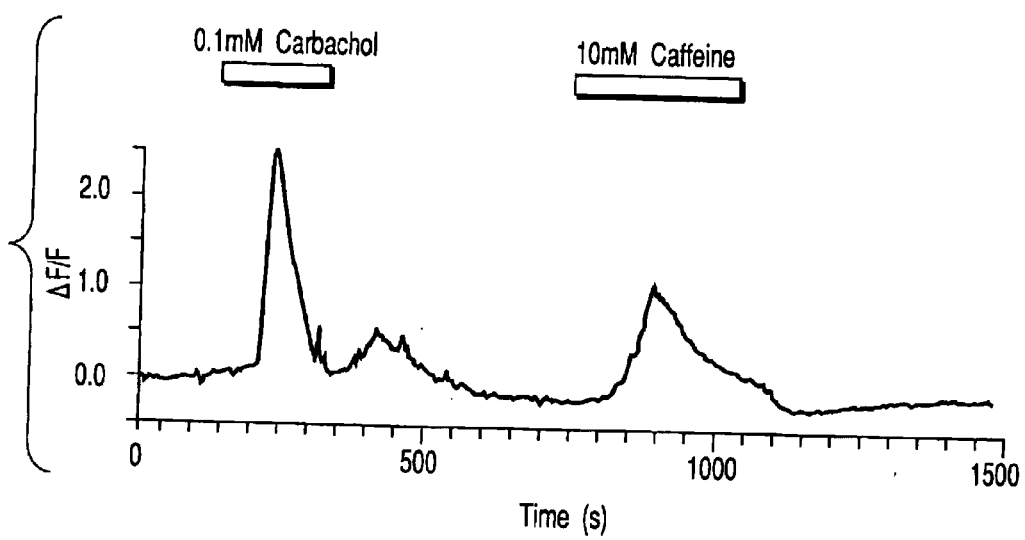
FIG. 4 shows a profile of the fluorescence intensity of a calcium sensor protein expressing in a skeletal muscle cell, which changes in response to carbachol and caffeine.

Similarly, a factor such as carbachol (0.1 mM) or caffeine (10 mM), which is known to increase the intracellular calcium ion concentration, is added to the skeletal muscle primary cultured cells expressing a calcium sensor (G85). The profile of the reaction is shown in FIG. 4. The change amount ($\Delta F/F$) of fluorescence in response to carbachol comes up to about 2.5, and the change amount ($\Delta F/F$) of fluorescence in response to caffeine reaches about 1.1, which is similar to the result of FIG. 3.

Figure 5:
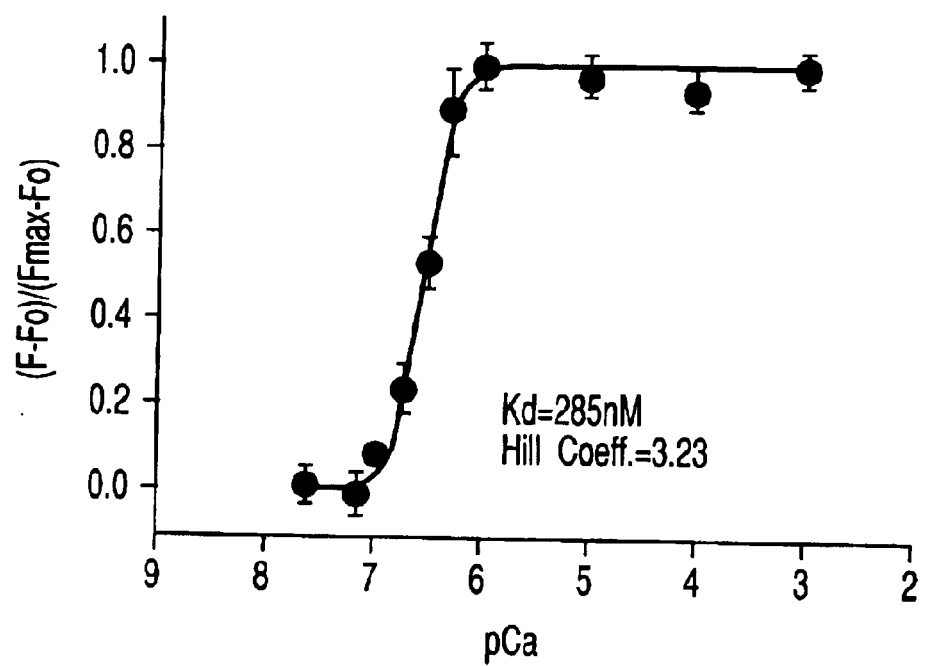
FIG. 5 is a graph showing the relationship between the calcium concentration and the fluorescence intensity.

Furthermore, the relationship between the calcium concentration and the fluorescence amount of the calcium sensor (G85) is shown in the graph of FIG. 5. The G85 is prepared by using E. coli. As shown in FIG. 5, the calcium sensor protein of the present invention exhibits extremely high calcium sensitivity. This sensitivity is about 30 times as high as that of a calcium-sensitive protein consisting of a single GFP described in the column of "BACKGROUND OF THE INVENTION".

As described above, it is demonstrated that the calcium sensor of the present invention has highly efficient performance as a sensor.

EXAMPLES

Method of Preparing Calcium Sensor and Method of Using the Calcium Sensor

Construction of pN1-G3 Encoding a Probe No. G3

1. Smooth Muscle Myosin Light Chain Kinase M13

The fragment M13 (Sequence ID No:6) of smooth muscle myosin light chain kinase was prepared using the following synthetic primers which have been synthesized by Katayama Chemical. More specifically, PCR was performed using the following two primers as templates and primers, thereby synthesizing the fragment M13 of smooth muscle myosin light chain kinase.

```
smMLCKM13-1 primer:
GCGCTAGCCGCCACCATGGGTACCTCATCACGTCGTAAGTGGAATAAGACAGGTCACGCAGTCAGA    (Sequence ID No: 9)

smMLCKM13-2 primer:
GGCGCGGCCGCTCAACTAGTTGAGCTCAGCCGACCTATAGCTCTGACTGCGTGACCTGTCTT    (Sequence ID No: 10)
```

The reaction mixture obtained by PCR was subjected to agarose gel electrophoresis. A target PCR product was recovered from the gel, and digested with NheI and SpeI restriction enzymes, to obtain a PCR fragment 1.

2. Modified GFP (i.e., Circularly Permutated Enhanced GFP: cpEGFP)

PCR was performed using the following primers and a plasmid pEGFP-N1 (available from Clontech) containing GFP-encoding cDNA as a template.

```
EGFP-31 primer:                    (Sequence ID No: 11)
GGACGCGTACTAGTAACGTCTATATCATGGCCGAC EGFP-20 primer:                    (Sequence ID No: 12)
CCGGTACCGCCCTTGTACAGCTCGTCCATGCC
```

The reaction mixture obtained by PCR was subjected to agarose gel electrophoresis. A target PCR product was recovered from the gel, and digested with SpeI and KpnI restriction enzymes, to obtain a PCR fragment 2.

Similarly, PCR was performed using the following primers and a plasmid pEGFP-N1 as a template.

```
EGFP-21 primer:                    (Sequence ID No: 13)
GCGGTACCGGAGGGAGCATGGTGAGCAAGGGCGAGGAG EGFP-30 primer:                    (Sequence ID No: 14)
GGACGCGTCCCGTTGTACTCCAGCTTGTGCCC
```

The reaction mixture obtained by PCR was subjected to agarose gel electrophoresis. A target PCR product was recovered from the gel, and digested with KpnI and MluI restriction enzymes, to obtain a PCR fragment 3.

3. Calmodulin (CaM)

PCR was performed using the following primers to rat calmodulin and a plasmid rCaM encoding a rat calmodulin cDNA (Sequence ID No: 3; Accession No. M19312 (Mon M, 2000, Biochemistry 39, 1316–1323)) as a template.

```
rCaM-2 primer:                     (Sequence ID No: 15)
GGACGCGTGACCAACTGACTGAAGAGCAG rCaM-10 primer:                    (Sequence ID No: 16)
GCGCGGCCGCTCACTTCGCTGTCATCATTTGTAC
```

The reaction mixture obtained by PCR was subjected to agarose gel electrophoresis. A target PCR product was recovered from the gel, and digested with MluI and NotI restriction enzymes, to obtain a PCR fragment 4.

The four fragments obtained were linked stepwise with DNA ligase, and the ligated fragment was finally introduced into a pEGFP-N1 vector which was previously digested with NheI and NotI restriction enzymes.

More specifically, the above four types of PCR fragments were prepared as described below.

The primers used in each PCR were synthesized primers (Sawady and Katayama Chemical).

The conditions in each PCR were as follows.

| Template DNA | 1 μg |
| Two primers | 10 pmol for each |
| Reaction buffer (Stratagene) | 5 μL |
| Pfu enzyme (Stratagene) | 2 units |
| 2.5 mM dNTP (Takara) | 4 μL |

Water was added to adjust a total volume to 50 μL.

The reaction temperature in each PCR was as follows.

| |
| --- |
| 1) 94° C., 2 minutes, 1 cycle |
| 2) 94° C., 30 seconds |
| 55° C., 30 seconds |
| 72° C., 1 minute, 30 cycles |
| 3) 72° C., 2 minutes, 1 cycle |

The recovery of DNA from gel was performed by using DNA Fragment Purification Kit MagExtractor (Toyobo) in accordance with the manual attached to the kit.

The agarose gel electrophoresis was performed using 1% or 2% agarose gel (Agarose LE, Nakarai Tesque) and TAE buffer (4.98 g/L Tris base (Nakarai Tesque), 1.142 mL/L glacial acetic acid (Nakarai Tesque), and 2 mL/L of 0.5 M EDTA (pH 8)(Dojin).

The cleavage of DNA by restriction enzymes was performed using any of NheI, SpeI, MluI, and NotI (available from NEB) and buffer attached to the enzymes. Specifically, the enzymes (30 units for each), the buffer (10 μL), and water were added to 1–2 μg of DNA, to adjust the total amount of the reaction mixture to 100 μL, and then the resultant reaction mixture was reacted for 1–3 hours at 37° C. Thereafter, DNA was recovered by using DNA Fragment Purification Kit MagExtractor (Toyobo) in accordance with the manual attached to the kit.

The ligation reaction was performed using a DNA Ligation kit (Takara) in accordance with the manual attached to the kit.

E. coli HB101 (Takara) was used as a competent cell, and transformed by a calcium chloride method (Molecular Cloning A Laboratory Manual, 2nd Edition, by J. Sambrook, E. F. Fritsch, T. Maniatis, Cold Spring Harbor Laboratory Press, 1989).

The recovery of the plasmid from E. coli was performed by using QIAprep Spin Miniprep kit (Qiagen) in accordance with the manual attached to the kit.

Introduction of Plasmid to Cells:

cDNA (that is, the plasmid recovered from E. coli) was introduced into HEK 293 cells (American Type Culture Collection) placed on a cover glass of 5×10 mm, by the use of a Superfect transfection reagent (Qiagen) in accordance with the manual attached thereto. The HEK 293 cells used herein were previously incubated in Dulbecco's modified Eagle medium (Gibuco BRL) containing 10% fetal bovine serum, penicillin (30 units/mL), and streptomycin (30 mg/mL).

More specifically, the cDNA (that is, the plasmid recovered from E. coli) was introduced as follows: First, for HEK cells cultured in 3 cm-dish, 12.5 μL of Superfect transfection reagent and 80 μL of serum-free Dulbecco's modified Eagle medium were added to 3 μg of the cDNA (3 μL). The resultant reaction mixture was allowed to stand still at room temperature for 10 minutes. Thereafter, to the reaction mixture, 800 μL of serum-containing Dulbecco's modified Eagle medium was added. The resultant reaction mixture was added to the HEK cells which was previously washed once with a phosphate buffer, and then the HEK cells were incubated for 2 hours at 37° C. The incubated HEK cells were washed once with the phosphate buffer. Thereafter, the Dulbecco's modified Eagle medium containing 10% fetal bovine serum was added to the HEK cells in an appropriate amount (2 mL per 3 cm-dish), and the cells were incubated at 28° C. for 2–4 days. The obtained cells were used in experiments.

Measurement:

The cover glass having the obtained cultured cells attached thererto was placed in a chamber on a stage of microscope, and refluxed with HBS solution (107 mM NaCl, 6 mM KCl, 1.2 mM MgSO4, 2 mM CaCl2, 1.2 mM KH2PO4, 11.5 mM glucose, and 20 mM HEPES pH 7.4 (purchased from Nakarai Tesque, Katayama Chemical, HEPES: 2-[4-(2-Hydroxyethyl)-1-piperazinyl] ethanesulfonic acid, Dojin)). 100 µM of adenosine 3'-phosphate (ATP, Sigma) or 100 µM of carbachol (Sigma) was dissolved in HBS, and the resultant ATP or carbachol solution was supplied to the cells by reflux. Using a Leica TCS-NT laser microscope, the cells were excited at a wavelength of 488 nm, and the emitted fluorescence was recorded at a wavelength of 525 nm.

(Effects of the Invention)

As explained in the foregoing, the method of producing a biosensor protein of the present invention can be applied to the development of various types of biosensors. Also, it is expected that a high-performance biosensor can be developed in a short period by using the method of producing a biosensor protein of the present invention.

The change amount in the signal intensity of the calcium sensor produced by using the method is sufficiently large to be observed by the naked eye. The calcium sensitivity of the calcium sensor is improved to 30 times as large as that of a conventional calcium sensor. Furthermore, since the calcium sensor is a protein sensor, the sensor can be readily expressed in a cell by introducing the sensor-encoding gene into the cell. Furthermore, the present invention has the following advantages: A specific device and substance are not required for measurement, and a detector using an argon laser can be used. Also, a coenzyme is not required for measurement.

In addition, the calcium sensor developed herein can be incorporated into a instrument for measuring a calcium concentration, by the use of the sensor protein itself. Moreover, the animal, plant, tissue, organ, cell, or the like, to which the gene encoding a biosensor protein of the present invention is introduced, can be used in developing pharmaceutical and agricultural products.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A nucleic acid molecule encoding an artificial biosensor protein comprising the following sequences (a) to (h) sequentially from the N terminus:
   (a) Met-Gly-Thr or Met-Val-Asp (linker X);
   (b) a partial amino acid sequence of myosin light chain kinase protein (Ser—Ser-Arg—Arg-Lys-Trp-Asn-Lys-Thr-Gly-His-Ala-Val-Arg-Ala-Ile-Gly-Arg-Leu-Ser—Ser)(SEQ ID NO: 6);
   (c) Leu-Glu (linker Y);
   (d) the amino acid sequence from the 149th to 238th position of green fluorescent protein of SEQ ID NO: 2;
   (e) Gly—Gly-Thr-Gly—Gly-Ser (linker amino acid sequence; (amino acids 117 to 122 of SEQ ID NO: 8);
   (f) the amino acid sequence from the 1st to 144th position of green fluorescent protein of SEQ ID NO: 2;
   (g) Gly-Thr-Arg or Thr-Arg (linker Z); and
   (h) the amino acid sequence from the 2nd to 148th position of rat calmodulin protein of SEQ ID NO: 4 or the amino acid sequence from the $2^{nd}$ to the $148^{th}$ position of calmodulin protein mutant CaMCN, in which residues 82-148 and 9-75 of SEQ ID NO: 4 have been exchanged.

2. A nucleic acid molecule encoding an artificial biosensor protein comprising the following sequences (a) to (g) sequentially from the N terminus:
   (a) the amino acid sequence from the 1st to 144th position of green fluorescent protein of SEQ ID NO: 2;
   (b) Gly-Thr-Arg (linker A);
   (c) the amino acid sequence from the 2nd to 148th position of rat calmodulin protein of SEQ ID NO: 4;
   (d) Gly-Thr or Gly-Thr-Gly-Ser-Gly—Gly—Gly-Ser (linker B; SEQ ID NO: 17);

(e) a partial amino acid sequence of myosin light chain kinase protein (Ser—Ser-Arg—Arg-Lys-Trp-Asn-Lys-Thr-Gly-His-Ala-Val-Arg-Ala-Ile-Gly-Arg-Leu-Ser—Ser)(SEQ ID NO: 6;

(f) Thr-Ser (linker C);

(g) the amino acid sequence from the 149th to 238th position of green fluorescent protein of SEQ ID NO: 2.

3. A nucleic acid molecule encoding an artificial biosensor protein comprising the following sequences (a) to (h) sequentially from the N terminus:

(a) Met-Gly-Thr or Met-Val-Asp (linker X);

(b) a partial amino acid sequence of myosin light chain kinase protein (Ser—Ser-Arg—Arg-Lys-Trp-Asn-Lys-Thr-Gly-His-Ala-Val-Arg-Ala-Ile-Gly-Arg-Leu-Ser—Ser)(SEQ ID NO: 6);

(c) an amino acid sequence that is selected from the group consisting of Thr-Ser, Gly-Ser, Leu-Glu, Thr-Tyr, Thr-Asp, Thr-Cys, Thr-Phe, Thr-Met, Thr—Thr, Thr-Glu, Thr-His and Thr-Leu (linker Y);

(d) the amino acid sequence from the 149th to 238th position of green fluorescent protein of SEQ ID) NO: 2;

(e) Gly—Gly-Thr-Gly—Gly-Ser (linker amino acid sequence; amino acids 117 to 122 of SEQ ID NO: 8);

(f) the amino acid sequence from the 1st to 144th position of green fluorescent protein of SEQ ID NO: 2;

(g) Gly-Thr-Arg or Thr-Arg (linker Z); and (h) the amino acid sequence from the 2nd to 148th position of rat calmodulin protein of SEQ ID NO: 4 or the amino acid sequence from the 2nd to 148th position of calmodulin protein mutant CaMCN, in which residues 82-148 and 9-75 of SEQ ID NO: 4 have been exchanged.

4. A nucleic acid molecule encoding an artificial biosensor protein comprising the following sequences (a) to (h) sequentially from the N terminus:

(a) Met-Gly-Thr or Met-Val-Asp (linker X);

(b) a partial amino acid sequence of myosin light chain kinase protein (Ser—Ser-Arg—Arg-Lys-Trp-Asn-Lys-Thr-Gly-His-Ala-Val-Arg-AJa-Ile-Gly-Arg-Leu-Ser—Ser) (SEQ ID NO: 6);

(c) an amino acid sequence that is selected from the group consisting of Thr-Ser, Gly-Ser, Leu-Glu, Thr-Tyr, Thr-Asp, Thr-Cys, Thr-Phe, Thr-Met, Thr—Thr, Thr-Glu, Thr-His and Thr-Leu (linker Y);

(d) an amino acid sequence from X-th to 238th position of green fluorescent protein of SEQ ID NO: 2 (where X is an arbitrary number from 148 to 150);

(e) Gly—Gly-Thr-Gly—Gly-Ser (linker amino acid sequence; amino acids 117 to 122 of SEQ ID NO: 8);

(f) an amino acid sequence from 1st to Y-th position of green fluorescent protein of SEQ ID NO: 2 (where Y is 140 when X is 148, Y is 144 or 147 when X is 149, or Y is 144 or 147 when X is 150);

(g) Gly-Thr-Arg or Thr-Arg (linker Z); and (h) the amino acid sequence from the $2^{nd}$ to $148^{th}$ position of rat calmodulin protein of SEQ ID NO: 4 or the amino acid sequence from the $2^{nd}$ to $148^{th}$ position of calmodulin protein mutant CaMCN, in which residues 82-148 and 9-75 of SEQ ID NO: 4 have been exchanged.

* * * * *

UNITED STATES PATENT AND TRADEMARK OFFICE
CERTIFICATE OF CORRECTION

PATENT NO. : 6,783,958 B2
DATED : August 31, 2004
INVENTOR(S) : Nakai

It is certified that error appears in the above-identified patent and that said Letters Patent is hereby corrected as shown below:

<u>Title page</u>,
Item [73], Assignee, should read:
-- [73]   Assignee: Okazaki National Research Institutes,
                          Okazaki (JP) --

Signed and Sealed this

Fourteenth Day of December, 2004

JON W. DUDAS
*Director of the United States Patent and Trademark Office*

SEQUENCE LISTING

<160> NUMBER OF SEQ ID NOS: 17

<210> SEQ ID NO 1
<211> LENGTH: 717
<212> TYPE: DNA
<213> ORGANISM: Aequorea victoria
<220> FEATURE:
<221> NAME/KEY: CDS
<222> LOCATION: (1)..(717)
<223> OTHER INFORMATION:

<400> SEQUENCE: 1

```
atg agc aag ggc gag gag ctg ttc acc ggg gtg gtg ccc atc ctg gtc       48
Met Ser Lys Gly Glu Glu Leu Phe Thr Gly Val Val Pro Ile Leu Val
1               5                   10                  15 gag ctg gac ggc gac gta aac ggc cac aag ttc agc gtg tcc ggc gag       96
Glu Leu Asp Gly Asp Val Asn Gly His Lys Phe Ser Val Ser Gly Glu
            20                  25                  30 ggc gag ggc gat gcc acc tac ggc aag ctg acc ctg aag ttc atc tgc      144
Gly Glu Gly Asp Ala Thr Tyr Gly Lys Leu Thr Leu Lys Phe Ile Cys
        35                  40                  45 acc acc ggc aag ctg ccc gtg ccc tgg ccc acc ctc gtg acc acc ctg      192
Thr Thr Gly Lys Leu Pro Val Pro Trp Pro Thr Leu Val Thr Thr Leu
    50                  55                  60 acc tac ggc gtg cag tgc ttc agc cgc tac ccc gac cac atg aag cag      240
Thr Tyr Gly Val Gln Cys Phe Ser Arg Tyr Pro Asp His Met Lys Gln
65                  70                  75                  80 cac gac ttc ttc aag tcc gcc atg ccc gaa ggc tac gtc cag gag cgc      288
His Asp Phe Phe Lys Ser Ala Met Pro Glu Gly Tyr Val Gln Glu Arg
                85                  90                  95 acc atc ttc ttc aag gac gac ggc aac tac aag acc cgc gcc gag gtg      336
Thr Ile Phe Phe Lys Asp Asp Gly Asn Tyr Lys Thr Arg Ala Glu Val
            100                 105                 110 aag ttc gag ggc gac acc ctg gtg aac cgc atc gag ctg aag ggc atc      384
Lys Phe Glu Gly Asp Thr Leu Val Asn Arg Ile Glu Leu Lys Gly Ile
```

-continued

```
                115                 120                 125
gac ttc aag gag gac ggc aac atc ctg ggg cac aag ctg gag tac aac       432
Asp Phe Lys Glu Asp Gly Asn Ile Leu Gly His Lys Leu Glu Tyr Asn
    130                 135                 140 tac aac agc cac aac gtc tat atc atg gcc gac aag cag aag aac ggc       480
Tyr Asn Ser His Asn Val Tyr Ile Met Ala Asp Lys Gln Lys Asn Gly
145                 150                 155                 160 atc aag gtg aac ttc aag atc cgc cac aac atc gag gac ggc agc gtg       528
Ile Lys Val Asn Phe Lys Ile Arg His Asn Ile Glu Asp Gly Ser Val
                165                 170                 175 cag ctc gcc gac cac tac cag cag aac acc ccc atc ggc gac ggc ccc       576
Gln Leu Ala Asp His Tyr Gln Gln Asn Thr Pro Ile Gly Asp Gly Pro
            180                 185                 190 gtg ctg ctg ccc gac aac cac tac ctg agc acc cag tcc gcc ctg agc       624
Val Leu Leu Pro Asp Asn His Tyr Leu Ser Thr Gln Ser Ala Leu Ser
        195                 200                 205 aaa gac ccc aac gag aag cgc gat cac atg gtc ctg ctg gag ttc gtg       672
Lys Asp Pro Asn Glu Lys Arg Asp His Met Val Leu Leu Glu Phe Val
    210                 215                 220 acc gcc gcc ggg atc act ctc ggc atg gac gag ctg tac aag taa           717
Thr Ala Ala Gly Ile Thr Leu Gly Met Asp Glu Leu Tyr Lys
225                 230                 235
```

<210> SEQ ID NO 2
<211> LENGTH: 238
<212> TYPE: PRT
<213> ORGANISM: Aequorea victoria

<400> SEQUENCE: 2

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220
```

```
Thr Ala Ala Gly Ile Thr Leu Gly Met Asp Glu Leu Tyr Lys
225                 230                 235

<210> SEQ ID NO 3
<211> LENGTH: 447
<212> TYPE: DNA
<213> ORGANISM: Rattus norvegicus
<220> FEATURE:
<221> NAME/KEY: CDS
<222> LOCATION: (1)..(444)
<223> OTHER INFORMATION:

<400> SEQUENCE: 3 gct gac caa ctg act gaa gag cag atc gca gaa ttc aaa gaa gct ttc      48
Ala Asp Gln Leu Thr Glu Glu Gln Ile Ala Glu Phe Lys Glu Ala Phe
1               5                   10                  15 tcc cta ttt gac aag gac ggg gat ggg aca ata aca acc aag gag ctg      96
Ser Leu Phe Asp Lys Asp Gly Asp Gly Thr Ile Thr Thr Lys Glu Leu
            20                  25                  30 ggg acg gtg atg cgg tct ctg ggg cag aac ccc aca gaa gca gag ctg     144
Gly Thr Val Met Arg Ser Leu Gly Gln Asn Pro Thr Glu Ala Glu Leu
        35                  40                  45 cag gac atg atc aat gaa gta gat gcc gac ggt aat ggc aca atc gac     192
Gln Asp Met Ile Asn Glu Val Asp Ala Asp Gly Asn Gly Thr Ile Asp
    50                  55                  60 ttc cct gaa ttc ctg aca atg atg gca aga aaa atg aaa gac aca gac     240
Phe Pro Glu Phe Leu Thr Met Met Ala Arg Lys Met Lys Asp Thr Asp
65                  70                  75                  80 agt gaa gaa gaa att aga gaa gcg ttc cgt gtg ttt gat aag gat ggc     288
Ser Glu Glu Glu Ile Arg Glu Ala Phe Arg Val Phe Asp Lys Asp Gly
                85                  90                  95 aat ggc tac atc agt gca gca gag ctt cgc cac gtg atg aca aac ctt     336
Asn Gly Tyr Ile Ser Ala Ala Glu Leu Arg His Val Met Thr Asn Leu
            100                 105                 110 gga gag aag tta aca gat gaa gag gtt gat gaa atg atc agg gaa gca     384
Gly Glu Lys Leu Thr Asp Glu Glu Val Asp Glu Met Ile Arg Glu Ala
        115                 120                 125 gac atc gat ggg gat ggt cag gta aac tac gaa gag ttt gta caa atg     432
Asp Ile Asp Gly Asp Gly Gln Val Asn Tyr Glu Glu Phe Val Gln Met
    130                 135                 140 atg aca gcg aag tga                                                  447
Met Thr Ala Lys
145

<210> SEQ ID NO 4
<211> LENGTH: 148
<212> TYPE: PRT
<213> ORGANISM: Rattus norvegicus

<400> SEQUENCE: 4

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80
```

```
Ser Glu Glu Glu Ile Arg Glu Ala Phe Arg Val Phe Asp Lys Asp Gly
            85                  90                  95

Asn Gly Tyr Ile Ser Ala Ala Glu Leu Arg His Val Met Thr Asn Leu
            100                 105                 110

Gly Glu Lys Leu Thr Asp Glu Val Asp Glu Met Ile Arg Glu Ala
            115                 120                 125

Asp Ile Asp Gly Asp Gly Gln Val Asn Tyr Glu Glu Phe Val Gln Met
        130                 135                 140

Met Thr Ala Lys
145

<210> SEQ ID NO 5
<211> LENGTH: 63
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(63)
<223> OTHER INFORMATION:

<400> SEQUENCE: 5 tca tca cgt cgt aag tgg aat aag aca ggt cac gca gtc aga gct ata      48
Ser Ser Arg Arg Lys Trp Asn Lys Thr Gly His Ala Val Arg Ala Ile
1               5                   10                  15 ggt cgg ctg agc tca                                                  63
Gly Arg Leu Ser Ser
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic DNA

<400> SEQUENCE: 6

Ser Ser Arg Arg Lys Trp Asn Lys Thr Gly His Ala Val Arg Ala Ile
1               5                   10                  15

Gly Arg Leu Ser Ser
            20

<210> SEQ ID NO 7
<211> LENGTH: 1251
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(1248)
<223> OTHER INFORMATION:

<400> SEQUENCE: 7 atg gtc gac tca tca cgt cgt aag tgg aat aag aca ggt cac gca gtc      48
Met Val Asp Ser Ser Arg Arg Lys Trp Asn Lys Thr Gly His Ala Val
1               5                   10                  15 aga gct ata ggt cgg ctg agc tca ctc gag aac gtc tat atc atg gcc     96
Arg Ala Ile Gly Arg Leu Ser Ser Leu Glu Asn Val Tyr Ile Met Ala
            20                  25                  30 gac aag cag aag aac ggc atc aag gtg aac ttc aag atc cgc cac aac    144
Asp Lys Gln Lys Asn Gly Ile Lys Val Asn Phe Lys Ile Arg His Asn
        35                  40                  45
```

```
atc gag gac ggc agc gtg cag ctc gcc gac cac tac cag cag aac acc      192
Ile Glu Asp Gly Ser Val Gln Leu Ala Asp His Tyr Gln Gln Asn Thr
     50              55                  60 ccc atc ggc gac ggc ccc gtg ctg ctg ccc gac aac cac tac ctg agc      240
Pro Ile Gly Asp Gly Pro Val Leu Leu Pro Asp Asn His Tyr Leu Ser
65              70                  75                  80 acc cag tcc gcc ctg agc aaa gac ccc aac gag aag cgc gat cac atg      288
Thr Gln Ser Ala Leu Ser Lys Asp Pro Asn Glu Lys Arg Asp His Met
                85                  90                  95 gtc ctg ctg gag ttc gtg acc gcc gcc ggg atc act ctc ggc atg gac      336
Val Leu Leu Glu Phe Val Thr Ala Ala Gly Ile Thr Leu Gly Met Asp
            100                 105                 110 gag ctg tac aag ggc ggt acc gga ggg agc atg gtg agc aag ggc gag      384
Glu Leu Tyr Lys Gly Gly Thr Gly Gly Ser Met Val Ser Lys Gly Glu
        115                 120                 125 gag ctg ttc acc ggg gtg gtg ccc atc ctg gtc gag ctg gac ggc gac      432
Glu Leu Phe Thr Gly Val Val Pro Ile Leu Val Glu Leu Asp Gly Asp
130                 135                 140 gta aac ggc cac aag ttc agc gtg tcc ggc gag ggc gag ggc gat gcc      480
Val Asn Gly His Lys Phe Ser Val Ser Gly Glu Gly Glu Gly Asp Ala
145                 150                 155                 160 acc tac ggc aag ctg acc ctg aag ttc atc tgc acc acc ggc aag ctg      528
Thr Tyr Gly Lys Leu Thr Leu Lys Phe Ile Cys Thr Thr Gly Lys Leu
                165                 170                 175 ccc gtg ccc tgg ccc acc ctc gtg acc acc ctg acc tac ggc gtg cag      576
Pro Val Pro Trp Pro Thr Leu Val Thr Thr Leu Thr Tyr Gly Val Gln
            180                 185                 190 tgc ttc agc cgc tac ccc gac cac atg aag cag cac gac ttc ttc aag      624
Cys Phe Ser Arg Tyr Pro Asp His Met Lys Gln His Asp Phe Phe Lys
        195                 200                 205 tcc gcc atg ccc gaa ggc tac gtc cag gag cgc acc atc ttc ttc aag      672
Ser Ala Met Pro Glu Gly Tyr Val Gln Glu Arg Thr Ile Phe Phe Lys
210                 215                 220 gac gac ggc aac tac aag acc cgc gcc gag gtg aag ttc gag ggc gac      720
Asp Asp Gly Asn Tyr Lys Thr Arg Ala Glu Val Lys Phe Glu Gly Asp
225                 230                 235                 240 acc ctg gtg aac cgc atc gag ctg aag ggc atc gac ttc aag gag gac      768
Thr Leu Val Asn Arg Ile Glu Leu Lys Gly Ile Asp Phe Lys Glu Asp
                245                 250                 255 ggc aac atc ctg ggg cac aag ctg gag tac aac acg cgt gac caa ctg      816
Gly Asn Ile Leu Gly His Lys Leu Glu Tyr Asn Thr Arg Asp Gln Leu
            260                 265                 270 act gaa gag cag atc gca gaa ttc aaa gaa gct ttc tcc cta ttt gac      864
Thr Glu Glu Gln Ile Ala Glu Phe Lys Glu Ala Phe Ser Leu Phe Asp
        275                 280                 285 aag gac ggg gat ggg aca ata aca acc aag gag ctg ggg acg gtg atg      912
Lys Asp Gly Asp Gly Thr Ile Thr Thr Lys Glu Leu Gly Thr Val Met
290                 295                 300 cgg tct ctg ggg cag aac ccc aca gaa gca gag ctg cag gac atg atc      960
Arg Ser Leu Gly Gln Asn Pro Thr Glu Ala Glu Leu Gln Asp Met Ile
305                 310                 315                 320 aat gaa gta gat gcc gac ggt aat ggc aca atc gac ttc cct gaa ttc      1008
Asn Glu Val Asp Ala Asp Gly Asn Gly Thr Ile Asp Phe Pro Glu Phe
                325                 330                 335 ctg aca atg atg gca aga aaa atg aaa gac aca gac agt gaa gaa gaa      1056
Leu Thr Met Met Ala Arg Lys Met Lys Asp Thr Asp Ser Glu Glu Glu
            340                 345                 350 att aga gaa gcg ttc cgt gtg ttt gat aag gat ggc aat ggc tac atc      1104
Ile Arg Glu Ala Phe Arg Val Phe Asp Lys Asp Gly Asn Gly Tyr Ile
        355                 360                 365
```

```
agt gca gca gag ctt cgc cac gtg atg aca aac ctt gga gag aag tta      1152
Ser Ala Ala Glu Leu Arg His Val Met Thr Asn Leu Gly Glu Lys Leu
370                 375                 380 aca gat gaa gag gtt gat gaa atg atc agg gaa gca gac atc gat ggg      1200
Thr Asp Glu Glu Val Asp Glu Met Ile Arg Glu Ala Asp Ile Asp Gly
385                 390                 395                 400 gat ggt cag gta aac tac gaa gag ttt gta caa atg atg aca gcg aag      1248
Asp Gly Gln Val Asn Tyr Glu Glu Phe Val Gln Met Met Thr Ala Lys
                405                 410                 415 tga                                                                   1251

<210> SEQ ID NO 8
<211> LENGTH: 416
<212> TYPE: PRT
<213> ORGANISM: Artificial Sequence
<220> FEATURE:
<223> OTHER INFORMATION: Synthetic DNA

<400> SEQUENCE: 8

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Met Ala
                20                  25                  30

Asp Lys Gln Lys Asn Gly Ile Lys Val Asn Phe Lys Ile Arg His Asn
            35                  40                  45

Ile Glu Asp Gly Ser Val Gln Leu Ala Asp His Tyr Gln Gln Asn Thr
        50                  55                  60

Pro Ile Gly Asp Gly Pro Val Leu Leu Pro Asp Asn His Tyr Leu Ser
65                  70                  75                  80

Thr Gln Ser Ala Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Thr Gly Gly Ser Met Val Ser Lys Gly Glu
        115                 120                 125

Glu Leu Phe Thr Gly Val Val Pro Ile Leu Val Glu Leu Asp Gly Asp
    130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
                165                 170                 175

Pro Val Pro Trp Pro Thr Leu Val Thr Thr Leu Thr Tyr Gly Val Gln
            180                 185                 190

Cys Phe Ser Arg Tyr Pro Asp His Met Lys Gln His Asp Phe Phe Lys
        195                 200                 205

Ser Ala Met Pro Glu Gly Tyr Val Gln Glu Arg Thr Ile Phe Phe Lys
    210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
                245                 250                 255

Gly Asn Ile Leu Gly His Lys Leu Glu Tyr Asn Thr Arg Asp Gln Leu
            260                 265                 270

Thr Glu Glu Gln Ile Ala Glu Phe Lys Glu Ala Phe Ser Leu Phe Asp
        275                 280                 285
```

| Lys | Asp | Gly | Asp | Gly | Thr | Ile | Thr | Thr | Lys | Glu | Leu | Gly | Thr | Val | Met |
|---|---|---|---|---|---|---|---|---|---|---|---|---|---|---|---|
| 290 | | | | | 295 | | | | | 300 | | | | | |

| Arg | Ser | Leu | Gly | Gln | Asn | Pro | Thr | Glu | Ala | Glu | Leu | Gln | Asp | Met | Ile |
|---|---|---|---|---|---|---|---|---|---|---|---|---|---|---|---|
| 305 | | | | | 310 | | | | | 315 | | | | | 320 |

| Asn | Glu | Val | Asp | Ala | Asp | Gly | Asn | Gly | Thr | Ile | Asp | Phe | Pro | Glu | Phe |
|---|---|---|---|---|---|---|---|---|---|---|---|---|---|---|---|
| | | | | 325 | | | | | 330 | | | | | 335 | |

| Leu | Thr | Met | Met | Ala | Arg | Lys | Met | Lys | Asp | Thr | Asp | Ser | Glu | Glu | Glu |
|---|---|---|---|---|---|---|---|---|---|---|---|---|---|---|---|
| | | | 340 | | | | | 345 | | | | | 350 | | |

| Ile | Arg | Glu | Ala | Phe | Arg | Val | Phe | Asp | Lys | Asp | Gly | Asn | Gly | Tyr | Ile |
|---|---|---|---|---|---|---|---|---|---|---|---|---|---|---|---|
| | | 355 | | | | | 360 | | | | | 365 | | | |

| Ser | Ala | Ala | Glu | Leu | Arg | His | Val | Met | Thr | Asn | Leu | Gly | Glu | Lys | Leu |
|---|---|---|---|---|---|---|---|---|---|---|---|---|---|---|---|
| | 370 | | | | | 375 | | | | | 380 | | | | |

| Thr | Asp | Glu | Glu | Val | Asp | Glu | Met | Ile | Arg | Glu | Ala | Asp | Ile | Asp | Gly |
|---|---|---|---|---|---|---|---|---|---|---|---|---|---|---|---|
| 385 | | | | | 390 | | | | | 395 | | | | | 400 |

| Asp | Gly | Gln | Val | Asn | Tyr | Glu | Glu | Phe | Val | Gln | Met | Met | Thr | Ala | Lys |
|---|---|---|---|---|---|---|---|---|---|---|---|---|---|---|---|
| | | | | 405 | | | | | 410 | | | | | 415 | |

<210> SEQ ID NO 9
<211> LENGTH: 66
<212> TYPE: DNA
<213> ORGANISM: Artificial Sequence
<220> FEATURE:
<223> OTHER INFORMATION: Synthetic DNA

<400> SEQUENCE: 9
gcgctagccg ccaccatggg tacctcatca cgtcgtaagt ggaataagac aggtcacgca    60
gtcaga    66

<210> SEQ ID NO 10
<211> LENGTH: 62
<212> TYPE: DNA
<213> ORGANISM: Artificial Sequence
<220> FEATURE:
<223> OTHER INFORMATION: Synthetic DNA

<400> SEQUENCE: 10
ggcgcggccg ctcaactagt tgagctcagc cgacctatag ctctgactgc gtgacctgtc    60
tt    62

<210> SEQ ID NO 11
<211> LENGTH: 35
<212> TYPE: DNA
<213> ORGANISM: Artificial Sequence
<220> FEATURE:
<223> OTHER INFORMATION: Synthetic DNA

<400> SEQUENCE: 11
ggacgcgtac tagtaacgtc tatatcatgg ccgac    35

<210> SEQ ID NO 12
<211> LENGTH: 32
<212> TYPE: DNA
<213> ORGANISM: Artificial Sequence
<220> FEATURE:
<223> OTHER INFORMATION: Synthetic DNA

<400> SEQUENCE: 12
ccggtaccgc ccttgtacag ctcgtccatg cc    32

<210> SEQ ID NO 13
<211> LENGTH: 38

```
<212> TYPE: DNA
<213> ORGANISM: Artificial Sequence
<220> FEATURE:
<223> OTHER INFORMATION: Synthetic DNA

<400> SEQUENCE: 13
gcggtaccgg agggagcatg gtgagcaagg gcgaggag                               38

<210> SEQ ID NO 14
<211> LENGTH: 32
<212> TYPE: DNA
<213> ORGANISM: Artificial Sequence
<220> FEATURE:
<223> OTHER INFORMATION: Synthetic DNA

<400> SEQUENCE: 14
ggacgcgtcc cgttgtactc cagcttgtgc cc                                    32

<210> SEQ ID NO 15
<211> LENGTH: 29
<212> TYPE: DNA
<213> ORGANISM: Artificial Sequence
<220> FEATURE:
<223> OTHER INFORMATION: Synthetic DNA

<400> SEQUENCE: 15
ggacgcgtga ccaactgact gaagagcag                                        29

<210> SEQ ID NO 16
<211> LENGTH: 34
<212> TYPE: DNA
<213> ORGANISM: Artificial Sequence
<220> FEATURE:
<223> OTHER INFORMATION: Synthetic DNA

<400> SEQUENCE: 16
gcgcggccgc tcacttcgct gtcatcattt gtac                                  34

<210> SEQ ID NO 17
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 17

Gly Thr Gly Ser Gly Gly Gly Ser
1               5
```